(12) United States Patent
Wu et al.

(10) Patent No.: US 10,695,092 B2
(45) Date of Patent: Jun. 30, 2020

(54) UTERINE MANIPULATOR

(71) Applicant: Conmed Corporation, Utica, NY (US)

(72) Inventors: Xiao Wu, Hamden, CT (US); Gregory Okoniewski, North Haven, CT (US); Ashley Holbrooks, New Haven, CT (US)

(73) Assignee: Conmed Corporation, Utica, NY (US)

( * ) Notice: Subject to any disclaimer, the term of this patent is extended or adjusted under 35 U.S.C. 154(b) by 181 days.

(21) Appl. No.: 15/899,427

(22) Filed: Feb. 20, 2018

(65) Prior Publication Data

US 2019/0254708 A1 Aug. 22, 2019

(51) Int. Cl.
| | |
|---|---|
| *A61B 17/42* | (2006.01) |
| *A61B 17/12* | (2006.01) |
| *A61M 25/10* | (2013.01) |
| *A61M 39/20* | (2006.01) |
| *A61B 90/00* | (2016.01) |

(Continued)

(52) U.S. Cl.
CPC .... *A61B 17/4241* (2013.01); *A61B 17/12099* (2013.01); *A61B 17/12181* (2013.01); *A61M 25/10* (2013.01); *A61M 39/20* (2013.01); *A61B 2017/00292* (2013.01); *A61B 2017/00526* (2013.01); *A61B 2017/00557* (2013.01); *A61B 2017/00862* (2013.01); *A61B 2017/00955* (2013.01); *A61B 2017/00995* (2013.01); *A61B 2017/4225* (2013.01); *A61B 2018/00559* (2013.01); *A61B 2090/062* (2016.02); *A61B 2090/0807* (2016.02);
(Continued)

(58) Field of Classification Search
CPC ........ A61B 17/12099; A61B 17/12181; A61B 17/4241; A61B 2017/00292; A61B 2017/00526; A61B 2017/00557; A61B 2017/00862; A61B 2017/00955; A61B 17/4225; A61B 2018/00559; A61B 2090/062; A61B 2090/0807; A61B 2217/007; A61M 25/10; A61M 39/20; A61M 2025/105; A61M 31/005
See application file for complete search history.

(56) References Cited

U.S. PATENT DOCUMENTS

| | | |
|---|---|---|
| 5,209,754 A | 5/1993 | Ahluwalia |
| 5,520,698 A | 5/1996 | Koh |

(Continued)

FOREIGN PATENT DOCUMENTS

CN 2917679 7/2007

OTHER PUBLICATIONS

Invitation to Pay Additional Fees International Application No. PCT/2017/036528, pp. 1-11, dated Aug. 31, 2017.

*Primary Examiner* — George J Ulsh
(74) *Attorney, Agent, or Firm* — Bond, Schoeneck & King, PLLC; Frederick J. M. Price

(57) ABSTRACT

A uterine manipulator device includes: an elongated cannulated tube having proximal and distal ends, a cervical cup positioned on the elongated cannulated tube with a top distal portion of a first diameter and a base proximal portion of a second smaller diameter, and an occluder assembly comprising an occluder positioned proximally from the cervical cup on the elongated cannulated tube, the occluder having a body with at least one primary rib and at least two secondary ribs, wherein a diameter of at least one secondary rib is smaller than the diameter of the primary rib.

29 Claims, 20 Drawing Sheets

(51) Int. Cl.
*A61B 17/00* (2006.01)
*A61M 31/00* (2006.01)
*A61B 18/00* (2006.01)

(52) U.S. Cl.
CPC ...... *A61B 2217/007* (2013.01); *A61M 31/005* (2013.01); *A61M 2025/105* (2013.01)

(56) References Cited

U.S. PATENT DOCUMENTS

| | | |
|---|---|---|
| D592,849 S | 5/2009 | Creelman |
| 8,292,901 B2 | 10/2012 | Auerbach et al. |
| 8,545,513 B2 | 10/2013 | Blair et al. |
| 8,568,423 B2 * | 10/2013 | Boebel ............... A61B 17/4241 606/119 |
| 8,603,105 B2 | 12/2013 | Sauer |
| 8,740,916 B2 | 6/2014 | Blair et al. |
| 8,939,988 B2 | 1/2015 | Auerbach et al. |
| D749,725 S | 2/2016 | Sauer |
| 9,327,097 B2 | 5/2016 | Ahluwalia |
| 9,522,252 B2 | 12/2016 | Ahluwalia et al. |
| 9,622,646 B2 | 4/2017 | Ouyang et al. |
| 9,636,144 B2 | 5/2017 | Parys et al. |
| 9,649,130 B2 | 5/2017 | Parys |
| 9,717,525 B2 | 8/2017 | Ahluwalia et al. |
| 2015/0127016 A1 | 5/2015 | Sauer |
| 2015/0257822 A1 | 9/2015 | Morozov |
| 2016/0270819 A1 * | 9/2016 | Ahluwalia ......... A61B 17/4241 |

\* cited by examiner

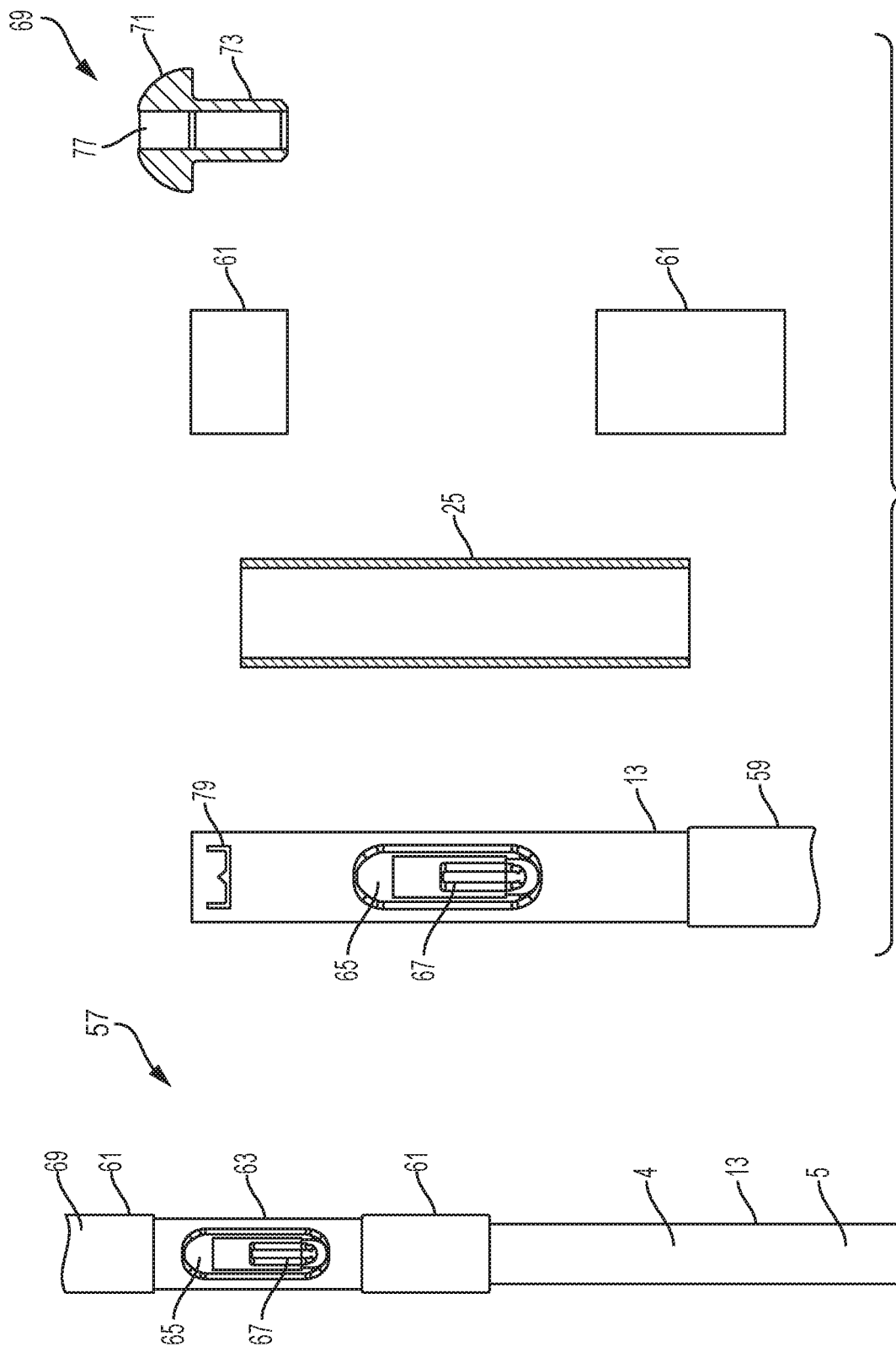

UTERINE MANIPULATOR

FIELD OF THE INVENTION

The present disclosure relates generally to devices and methods for manipulation of the uterus and cervix in surgical and diagnostic procedures.

BACKGROUND

Various conventional forms of uterine manipulators and vaginal cervical retractors are known. For example, U.S. Pat. No. 5,209,754 describes a vaginal cervical retractor generally consisting of a distal (to the medical practitioner using the device) half-length curved outer shaft (corresponding to the curve of the posterior pelvis) and a straight proximal half connected to a handle, an inner cap positioned within an outer cap and a circular disc located at the distal end of the outer tube, and an inner plastic tube positioned through the outer tube and the circular disc, inner cap and outer cap (which can include one cervical cup in certain conventional devices) with a balloon on the distal end. The vaginal cervical retractor is used to maneuver and visualize the uterus during various medical examinations and laparoscopic procedures while maintaining pneumoperitoneum. Such examinations and procedures include a complete, total laparoscopic hysterectomy, a partial laparoscopic hysterectomy, and a colpotomy. While the vaginal cervical retractor maneuvers the uterus during a complete, total laparoscopic hysterectomy, for example, by, in part, positioning and inflating the balloon within the uterine cavity, capturing the vaginal fornix in the inner cap, and maintaining the pneumoperitoneum by properly positioning the disc, a laparoscope can be inserted through a surgically formed incision in the wall of the patient's abdomen to allow for visualization of the peritoneal cavity and the uterus to assist with the hysterectomy. Other conventional forms of uterine manipulators and vaginal cervical retractors exist and contain similar features.

However, some conventional uterine manipulators and vaginal cervical retractors do not include a mechanism or structural configuration to sufficiently maintain pneumoperitoneum during a particular medical procedure (as described above). Additionally, some conventional uterine manipulators and vaginal cervical retractors do not include a configuration to sufficiently fit and retain the balloon on the distal end of the inner or manipulator tube. Indeed, the balloon of such conventional uterine manipulators and vaginal cervical retractors often bunches up during assembly implicating certain potential safety and lack of sterilization concerns during the particular medical procedure. Moreover, conventional uterine manipulators and vaginal cervical retractors do not include a mechanism to pass dye other than through a slit in the balloon, and use saline instead of gas to inflate the balloon.

Accordingly, there is a need in the art for improved devices and methods for manipulation of the uterus and cervix in surgical and diagnostic procedures including a mechanism or structural configuration to address each of these and other short comings of conventional devices.

Description of the Related Art Section Disclaimer: To the extent that specific patents/publications/products are discussed above in this Background Section or elsewhere in this Application, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Background Section and/or throughout the application, the descriptions/disclosures of which are all hereby incorporated by reference into this document in their respective entirety(ies).

SUMMARY OF THE INVENTION

The present disclosure is directed to inventive devices and methods for manipulation of the uterus and cervix in surgical and diagnostic procedures, which overcome the various problems with conventional devices (as discussed herein and below). A particular non-limiting goal of utilization of the embodiments and implementations herein is to provide a device for manipulation of the uterus and injection of fluids or gases during laparoscopic procedures such as laparoscopic assisted vaginal hysterectomy (LAVH), total laparoscopic hysterectomy (TLH), minilap, laparoscopic tubal occlusion or diagnostic laparoscopy (and other similar procedures as should be understood by a person of ordinary skill in the art in conjunction with a review of this disclosure), and for the maintenance of a pneumoperitoneum by sealing the vagina during such procedures. In brief, the uterine manipulator device of an embodiment allows a medical practitioner to more easily access key surgical targets in the pelvic cavity by creating clear visibility of surgical landmarks and superior mobility of the uterus maximizing safe operative margins from the pelvic wall. The device can be structured and/or configured to displace the cervix away from the ureters, displace the bladder anteriorially, define the dissecting plane of a colpotomy, and prevent loss of pneumoperitoneum during the colpotomy (as noted above). Applicant has recognized and appreciated that it would be beneficial for medical practitioners to be able to approach such procedures with a higher degree of confidence in performing a consistent, predictable and repeatable procedure.

Generally, in one aspect, a uterine manipulator device includes an elongated cannulated tube comprising a distal end and a proximal end; a cervical cup positioned on the elongated cannulated tube having a top distal portion of a first diameter and a base proximal portion of a second smaller diameter; and an occluder assembly comprising an occluder positioned proximally from the cervical cup on the elongated cannulated tube, the occluder having a body with at least one primary rib and at least two secondary ribs, wherein a diameter of at least one secondary rib is different than a diameter of the primary rib.

According to another aspect, a uterine manipulator device includes an elongated cannulated tube comprising a distal end and a proximal end, wherein laser marked reference graduations are positioned along an outside surface of the elongated cannulated tube; a cervical cup positioned on the elongated cannulated tube having a top distal portion of a first diameter and a base proximal portion of a second smaller diameter; and an occluder assembly comprising an occluder having a body positioned proximally from the cervical cup on the elongated cannulated tube.

According to a further aspect, a uterine manipulator device includes an elongated cannulated tube comprising a distal end and a proximal end; a cervical cup positioned on the elongated cannulated tube having a top distal portion of a first diameter and a base proximal portion of a second smaller diameter; and an intrauterine balloon comprising a distal end and a proximal end and being positioned on the distal end of the elongated cannulated tube, wherein the distal end and the proximal end of the intrauterine balloon are secured to the elongated cannulated tube with heat shrink material.

As used herein for purposes of the present disclosure, the terms "distal" and "proximal" are used to describe locations of embodiments of the device from the perspective of a medical practitioner using the device.

BRIEF DESCRIPTION OF THE DRAWINGS

The present invention will be more fully understood and appreciated by reading the following Detailed Description in conjunction with the accompanying drawings. The accompanying drawings illustrate only typical embodiments of the disclosed subject matter and are therefore not to be considered limiting of its scope, for the disclosed subject matter may admit to other equally effective embodiments.

Reference is now made briefly to the accompanying drawings, in which.

Figure 1:
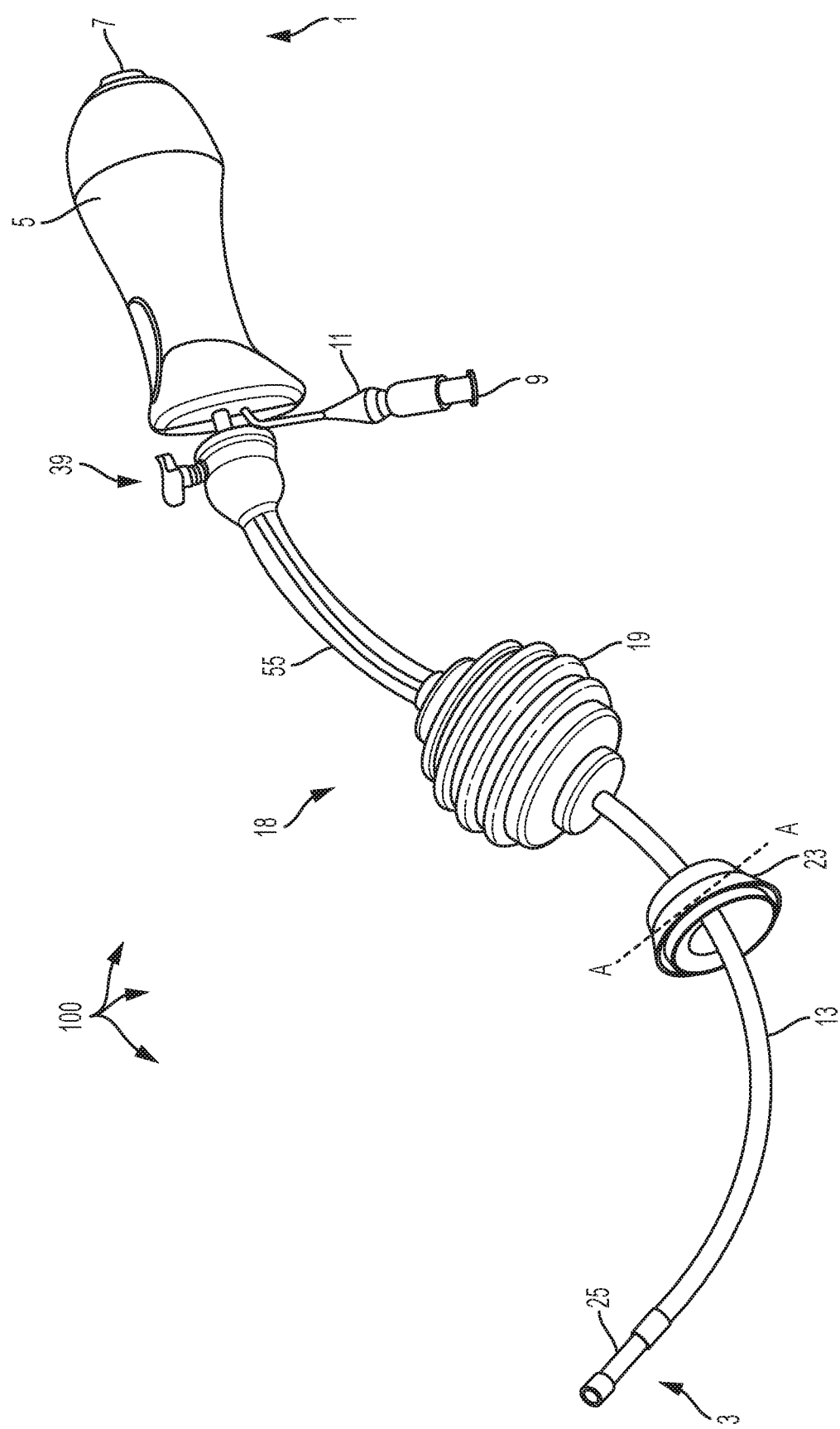
FIG. 1 is a top side perspective view of a fully assembled uterine manipulator device according to an embodiment.

Where applicable, like reference characters designate identical or corresponding components and units throughout the several views, which are not to scale unless otherwise indicated. Moreover, the embodiments disclosed herein may include elements that appear in one or more of the several views or in combinations of the several views.

DETAILED DESCRIPTION OF EMBODIMENTS

Referring to FIG. 1, in one embodiment, is a schematic representation of a uterine manipulator device 100. The uterine manipulator device 100 can include (from the proximal end 1 to the distal end 3) a handle 5, a dye injection port 7 positioned in the handle 5 (preferably through the proximal end, and communicatively coupled to an intrauterine balloon 25), an inflation valve 9 (communicatively coupled to the intrauterine balloon 25), to which a syringe (e.g., 10 cc syringe, not shown) can be attached, and a pilot balloon 11 are attached to the handle 5 (preferably through the distal end), and a cannulated manipulator tube 13. The cannulated manipulator tube 13 is curved at its distal end and is straight at its proximal end for easy introduction of the device 100, for manipulation of both retroverted and anteverted uteri, and for maintaining proper attitude of the uterus at the proximal end. The cannulated manipulator tube 13 is connected to the handle 5 (preferably at the distal end of the handle 5) and to the dye injection port 7, inflation valve 9, and pilot balloon 11 through the handle 5. The manipulator tube 13 is configured to anatomically conform to the angle of the sacral curve, and to allow for easy manipulation of the uterus. The handle 5, which can be smooth (as shown) and conform to a user's hand as a whole or provide for the positioning of all four fingers on one side and the thumb on the opposite side (which can include a gripping/non-smooth surface such as a plurality of raised portions or other non-smooth surface structure as should be appreciated by a person of skill in the art in conjunction with a review of this disclosure), allows for easy manipulation of the uterus up, down and sideways.

The uterine manipulator device 100 incorporates a system of manipulating/elevating mechanisms positioned on the manipulator tube 13 to provide manipulation of the uterus, and retraction and elevation of the cervix. These mechanisms may comprise a cervical cup 23 and an occluder assembly 18 including an occluder 19, a stem 55 and a locking assembly 39, each of which comprises a hole therethrough to facilitate movement along and positioning on the manipulator tube 13 (the occluder assembly 18 and the cervical cup 23 being able to be locked and unlocked in place and prevented from moving proximally on the manipulator tube 13 per the use of a locking assembly 39, shown in more detail and described below with respect to FIGS. 4-5). The cervical cup 23 is positioned on and adjacent to the distal end of the manipulator tube 13, and can include sites/holes for suturing positioned through the side of the cervical cup 23. The cervical cup 23 can include various volumes and diameters, examples of which are shown in Table 1 below:

TABLE 1

| Cervical Cup Volume | Cervical Cup | Cervical Cup Designation |
|---|---|---|
| 9.7 cm³ (0.59 in³) | 32 mm (1.26 in) | S |
| 14.3 cm³ (0.87 in³) | 34 mm (1.34 in) | M |
| 20.7 cm³ (1.26 in³) | 37 mm (1.46 in) | L |
| 26.7 cm³ (1.63 in³) | 40 mm (1.57 in) | XL |

Figure 2:
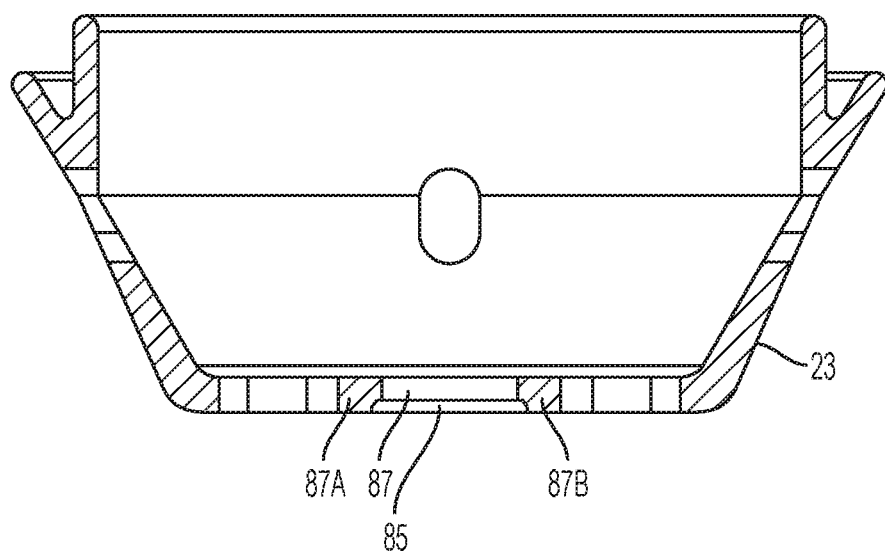
FIG. 2 is a schematic sectional representation of the cervical cup of the uterine manipulator device taken along A-A of FIG. 1 according to an embodiment.

Referring to FIG. 2, in one embodiment, is a schematic representation of the cervical cup 23 taken along A-A of FIG. 1. As shown, the cervical cup 23 tapers from a top distal portion with a first diameter to a base proximal portion with a second smaller diameter including a central hole 85 having a perimeter 87. The perimeter can be chamfered/angled away from the longitudinal axis A at the proximal end 87B, and can be straight/not angled with respect to the longitudinal axis A at the distal end 87A (the angling can be reversed). The chamfering of the perimeter aids in the movement of the cervical cup 23 along the manipulator tube 13. The straight/not angled perimeter portion aids in increasing the retention force of the cervical cup 23 on the manipulator tube 13 and in preventing detachment of the cup from the manipulator tube 13. Additionally, the hole 85 diameter can be decreased (from 2.15 cm to 2.05 cm). The combination of the straight/not angled perimeter portion and the narrowing of the diameter of the hole 85 significantly increases the retention force of the cervical cup 23 on the manipulator tube 13.

Figure 3A:
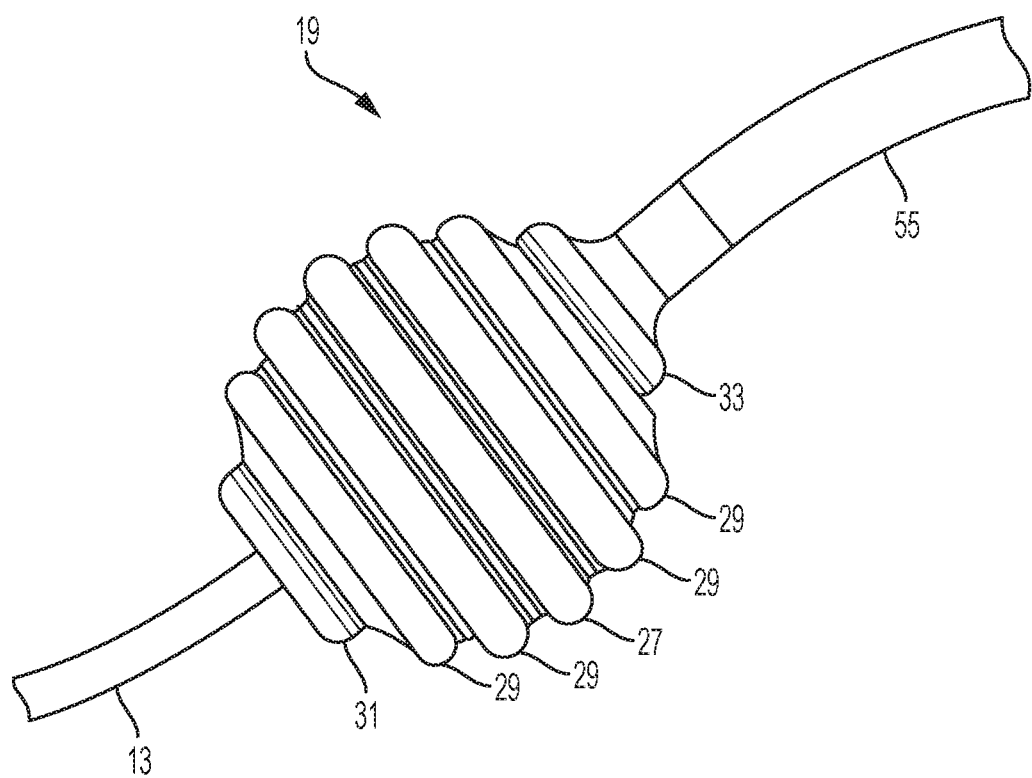
FIG. 3A is a side perspective view of an occluder of the uterine manipulator device according to an embodiment.

Referring now to FIG. 3A, there is shown a side view of an illustrative embodiment of the occluder 19 and stem 55 with the manipulator tube 13 positioned therethrough. A purpose of the occluder 19 is to keep gas (e.g., insufflation gas) in the exposed cavity to maintain insufflation of the cavity. Thus, the occluder 19 should preferably be relatively small (e.g., under 2.6" in diameter), easy to insert and to remove, and impermeable to gas. In one embodiment, the occluder 19 can be composed of open cell foam with a thin "skin" layer 28 (i.e. outer layer), which allows the occluder 19 to be easily compressible for proper positioning, and is configured to expand back to its original shape after it is properly positioned during use of the uterine manipulator (as should be understood by a person of ordinary skill in the art in conjunction with a review of this disclosure), but also to prevent leaks through the open cell foam. In one embodiment, the inner open cell foam and the outer layer can be composed of the same material. However, the outer skin layer can alternatively have a different material and/or density (e.g., higher density) and/or can be an area of different permeability than the inner open cell foam. For example, varying the temperature of the mold to prepare the occluder 19 can provide a thickening and more dense outer skin layer that can result in an increase in impermeability (not as porous) of the outer skin layer.

Still referring to FIG. 3A, the occluder 19 is spheroid shaped and comprises a plurality of ridges (or "ribs"). In the depicted embodiment, a primary rib 27 with the largest diameter is positioned approximately at the center of the occluder 19 and secondary ribs 29 positioned on either side taper away from the center such that the most distal secondary rib 31 and most proximal secondary rib 33 have the smallest diameter (forming an essentially symmetric design). This symmetric design makes the occluder 19 easier to insert and remove, while still performing the essential blocking/occlusion functionality of an occluder. In an alternative embodiment, all the secondary ribs 29 on either side of the primary rib 27 are smaller and/or equal sized, having approximately the same diameter. In the described embodiments, the secondary ribs 29 are structured not to interrupt the sealing ability of the primary rib 27 and to permit the best occlusion. Conventional sealing mechanisms are not symmetrical, and are usually entirely smooth (i.e., lacking ribs or ridges) and may taper without ribs.

Figure 3B:
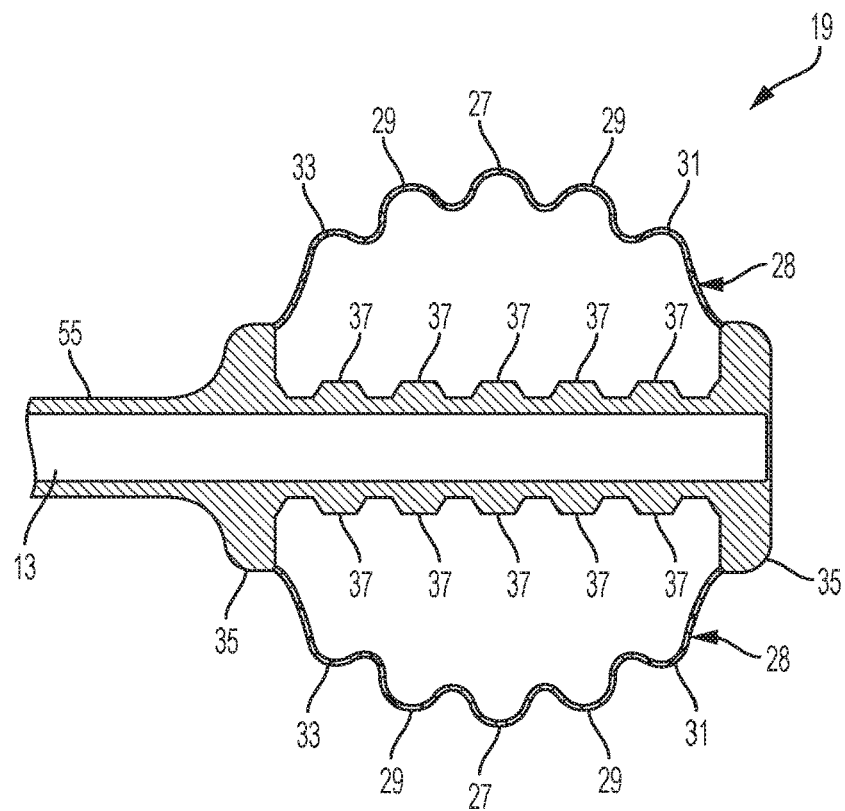
FIG. 3B is a side sectional view schematic representation of the occluder of the uterine manipulator device according to an embodiment.

Turning now to FIG. 3B, the occluder 19 may also comprise anti-pneumoccluder migration features on its distal and/or proximal sides, which are configured to prevent movement of the occluder 19 with respect to the stem 55 in the distal and proximal directions. In the depicted embodiment, the anti-migration features are "barbell" features 35. The barbell features 35 on the distal and proximal ends of the occluder 19 can be composed of hard plastic and are structured to maintain the open cell foam therebetween. The occluder 19 can also comprise a series of internal grooves 37, which can have a diameter less than or equal to 50% and preferably no greater than 25% of the smallest rib diameter of the occluder 19. The size of the internal grooves 37 aids in compressibility of the occluder 19 while also preventing migration of the occluder 19 (as discussed above). The barbell features 35 permit the occluder 19 to rotate about its central axis, while the internal grooves 37 can be configured (but don't have to be configured) to prevent the occluder 19 from freely migrating with or without additional structural features. The internal grooves 37 can also have structural features to prevent free rotation of the occluder 19.

Figure 3C:
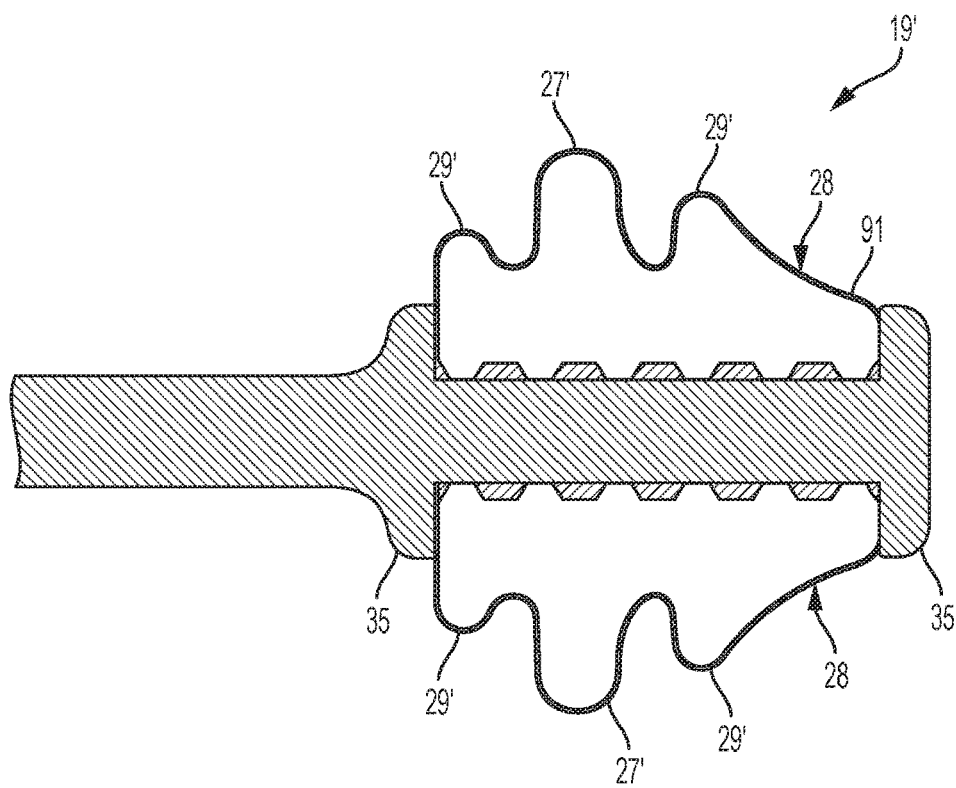
FIG. 3C is a schematic sectional representation of an occluder of a uterine manipulator device according to an alternative embodiment.

Referring to FIG. 3C, a schematic sectional representation of an occluder 19' according to an alternative embodiment is shown. Occluder 19' is shaped differently from occluder 19 in order to perform certain functions described herein. For example, the front/distal leading section 91 is conical in shape, narrower at the distal end and wider/thicker at the proximal end near secondary rib 29' allowing a natural dilation of the anatomy (as should be understood by a person of ordinary skill in the art in conjunction with a review of this disclosure). The primary rib 27' is centralized between two smaller secondary ribs 29', 29'. Each of the secondary ribs 29', 29', of which there could be two or more, can be of the same thickness or of different thicknesses from one or more of the other secondary ribs 29'. The primary rib 27' is spaced from each secondary rib 29', 29' to allow for primary rib 27' to at least partially collapse proximally during insertion, or distally upon removal. The primary rib 27' is bigger in diameter/thickness as compared to the secondary ribs 29', 29'. These secondary ribs 29', 29', which exist on either side of the primary rib 27', are configured and structured to provide additional sealing capability should the primary rib 27' leak or otherwise not fully perform as may be needed. However, secondary ribs 29', 29' are also configured to provide additional support to the primary rib 27' such that the secondary ribs 29', 29' are configured and structured to not allow the primary rib 27' to fully collapse down (aka acts as a prop), and thus prevents to the primary rib 27' from being ineffective.

Figure 3D:
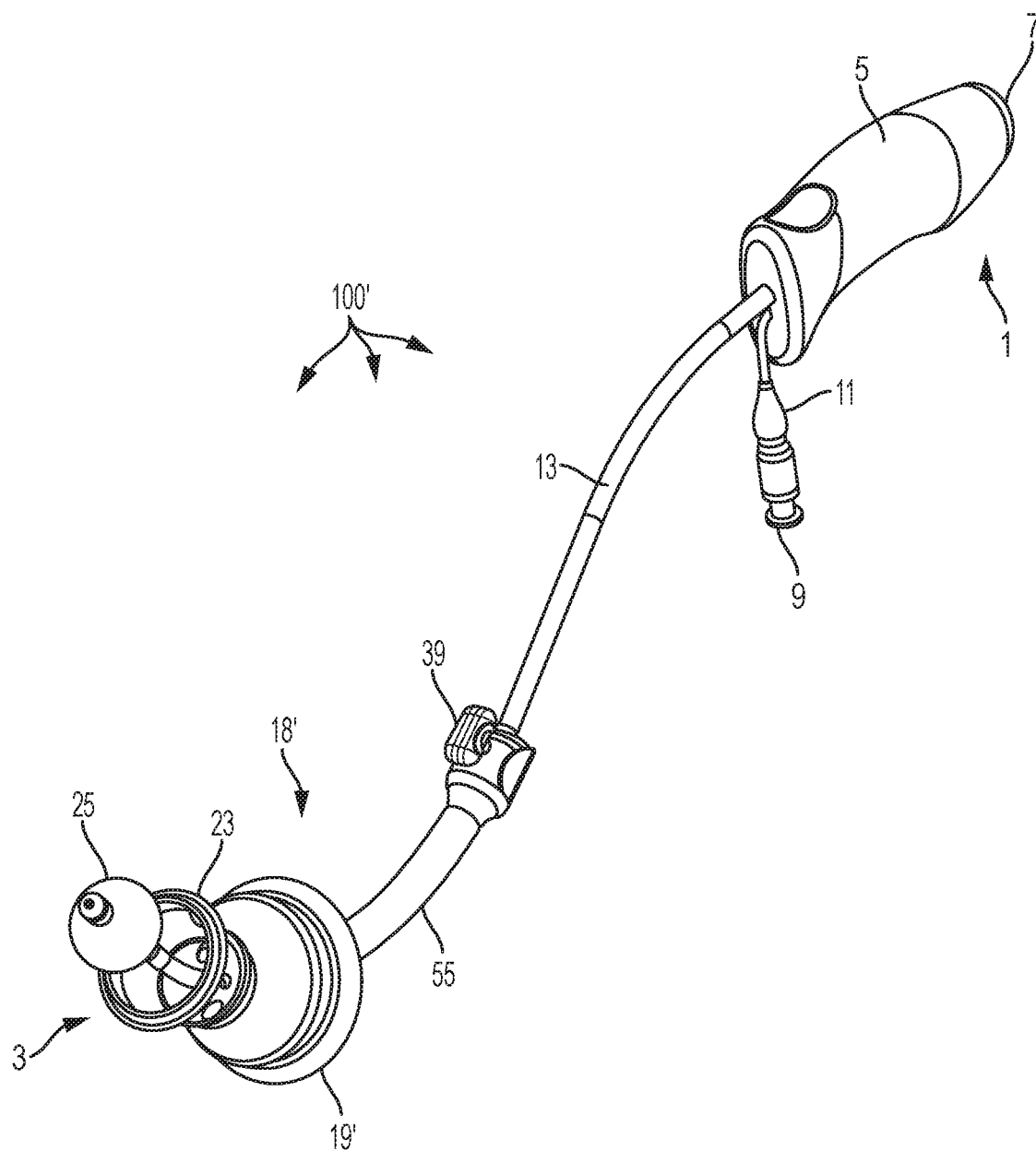
FIG. 3D is a perspective view of a uterine manipulator device according to an alternative embodiment.
Figure 3E:
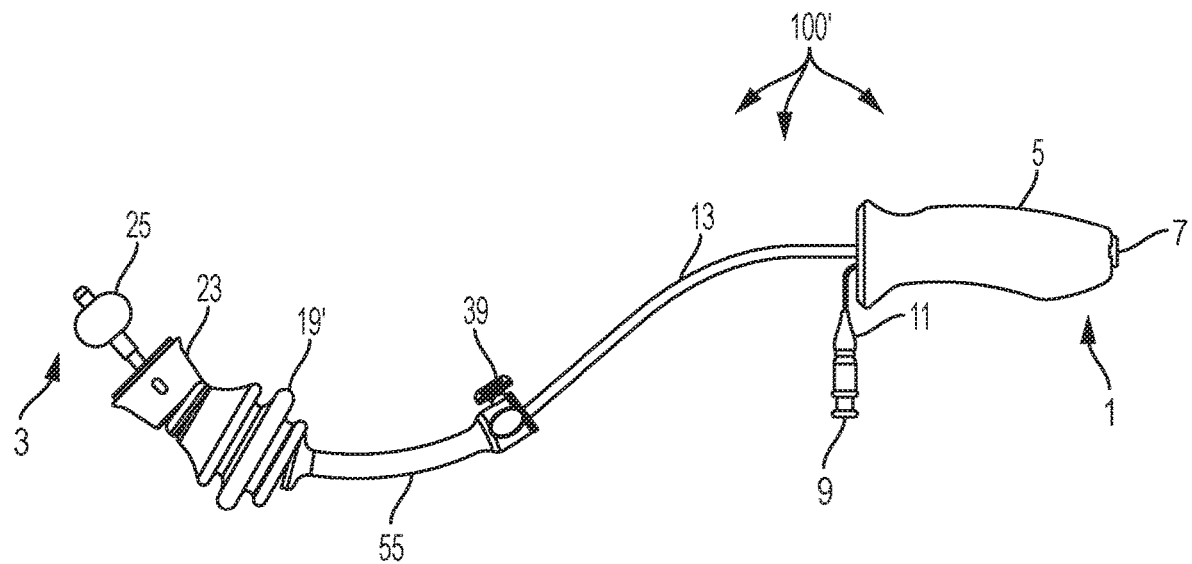
FIG. 3E a side view of a uterine manipulator device according to an alternative embodiment.
Figure 3F:
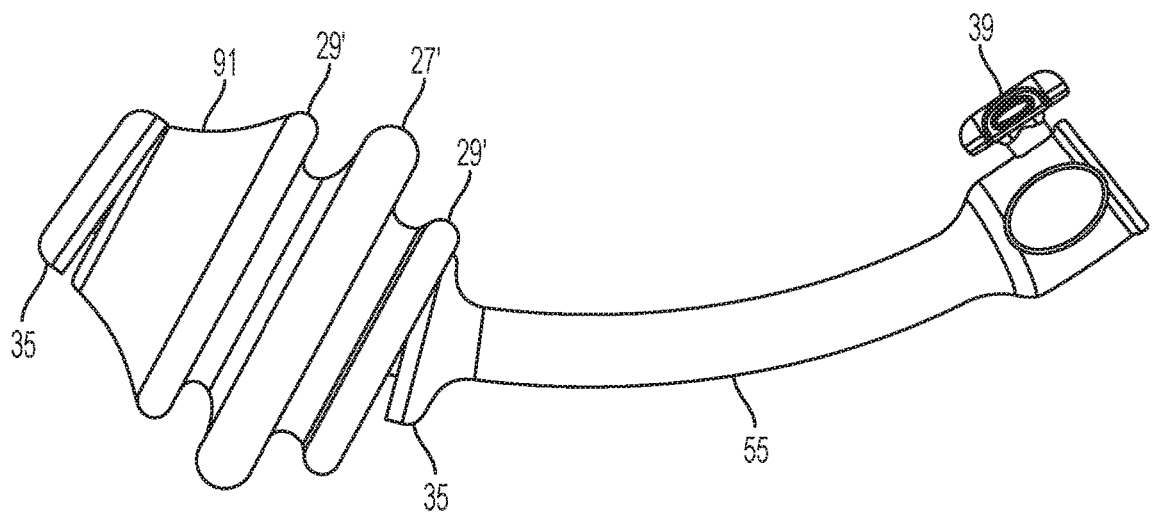
FIG. 3F is a side view of an occluder assembly of a uterine manipulator device according to an alternative embodiment.

Turning to FIG. 3D, a perspective view of a fully assembled uterine manipulator device 100' according to an alternative embodiment is shown. FIG. 3E is a side perspective view of fully assembled uterine manipulator device 100', and FIG. 3F is a side perspective view of an occluder assembly 18' including an occluder 19', according to an alternative embodiment. Uterine manipulator device 100' includes occluder 19', described above. All other elements of uterine manipulator device 100' are the same or similar to uterine manipulator device 100.

Figure 4:
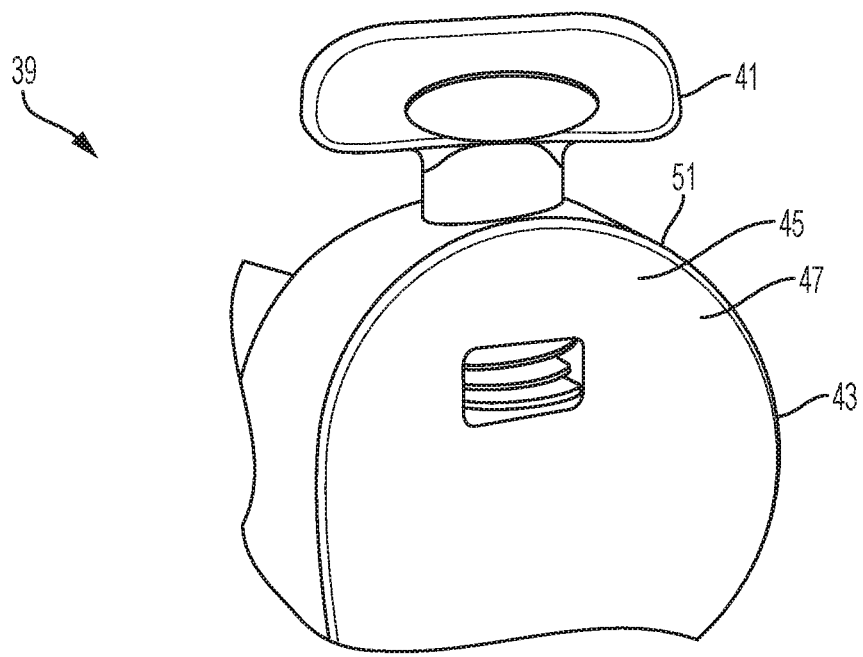
FIG. 4 is a close-up front view of a locking assembly of the uterine manipulator device according to an embodiment.

Turning now to FIG. 4, there is shown a close-up front view of the locking assembly 39. Once the occluder 19 is in the desired position to block gas from leaving the exposed cavity (as should be understood by a person of ordinary skill in the art in conjunction with a review of this disclosure), the occluder 19 should be locked in place (which also prevents proximal movement of the cervical cup 23). In the depicted embodiment, the locking assembly 39 includes a thumbscrew 41 in a collar 43 to secure the occluder 19 in the desired position along the manipulator tube 13. With conventional screws, the user does not know how deep the screw is in the collar and thus, when loosening the screw, the screw oftentimes falls out. To permit tightening and loosening of the screw without risking losing the screw, the thumbscrew 41 in the depicted embodiment is shown deformed. The thumbscrew 41 shown has normal features until the last two threads 45, 47. The intermediary threads 51 are spaced approximately equidistant. The last thread 47, however, is over-torqued such that there is virtually no pitch between the last two threads 45, 47. As there is no space between the last two threads 45, 47, the thumbscrew 41 cannot be entirely removed from the collar 43. Therefore, although the thumbscrew 41 can be loosened and tightened, it cannot be completely removed from the collar 43, preventing loss of the thumbscrew 41. The thumbscrew 41 shown in FIG. 4 may be created by first, putting the thumbscrew 41 in the collar 43 and second, deforming the thumbscrew 41 using a cold worked compression method (e.g., over-torquing the thumbscrew on an anvil). The collar 43 may then be put onto the device 100. Alternatively, other blocking mechanisms (e.g., washer, nut, plastic piece, other deformation of the screw) that are bigger than the hole that the screw is positioned through (or otherwise does not allow the screw to come out of the hole) are contemplated.

Figure 5:
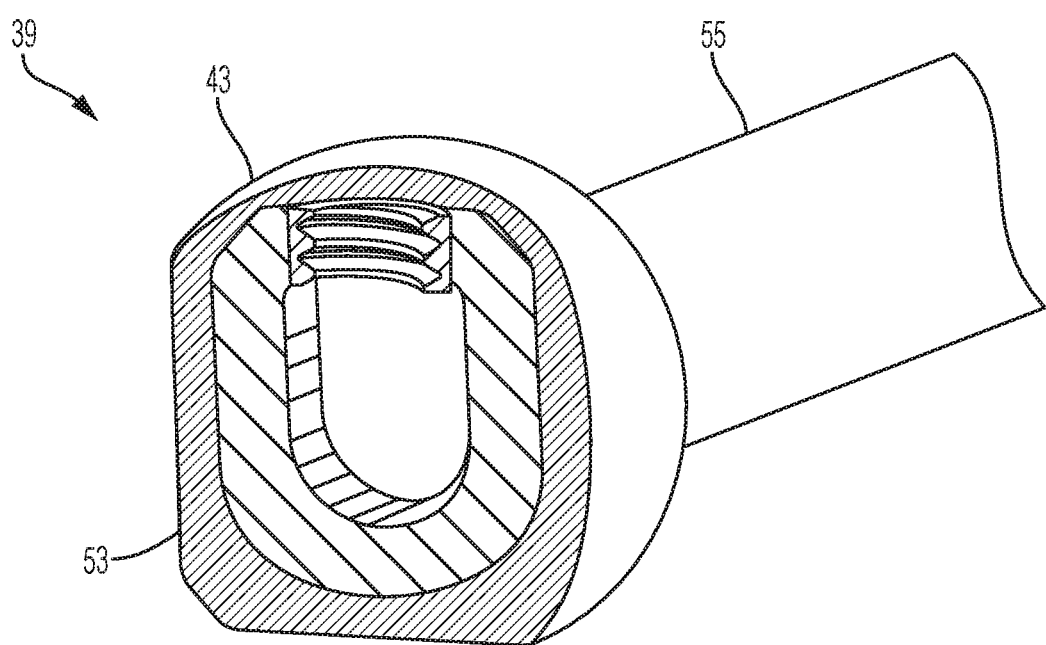
FIG. 5 is a close-up front view of locking assembly of the uterine manipulator device with the thumbscrew removed according to an embodiment.

Referring now to FIG. 5, a close-up front view of the collar 43 of the locking assembly 39 is shown. Traditionally, the collar 43 has a screw channel composed of soft santoprene material. The santoprene material is very elastic and deforms easily such that it could be pressed down until the screw bottoms out. In the depicted embodiment, however, the collar 43 has a ring 53 of hard plastic, polycarbonate, nylon, for example, overmolded into the screw channel. The ring 53 of hard plastic permits the thumbscrew 41 to push against it while maintaining the shape of the one-piece occluder stem 55 design.

Figure 6A:
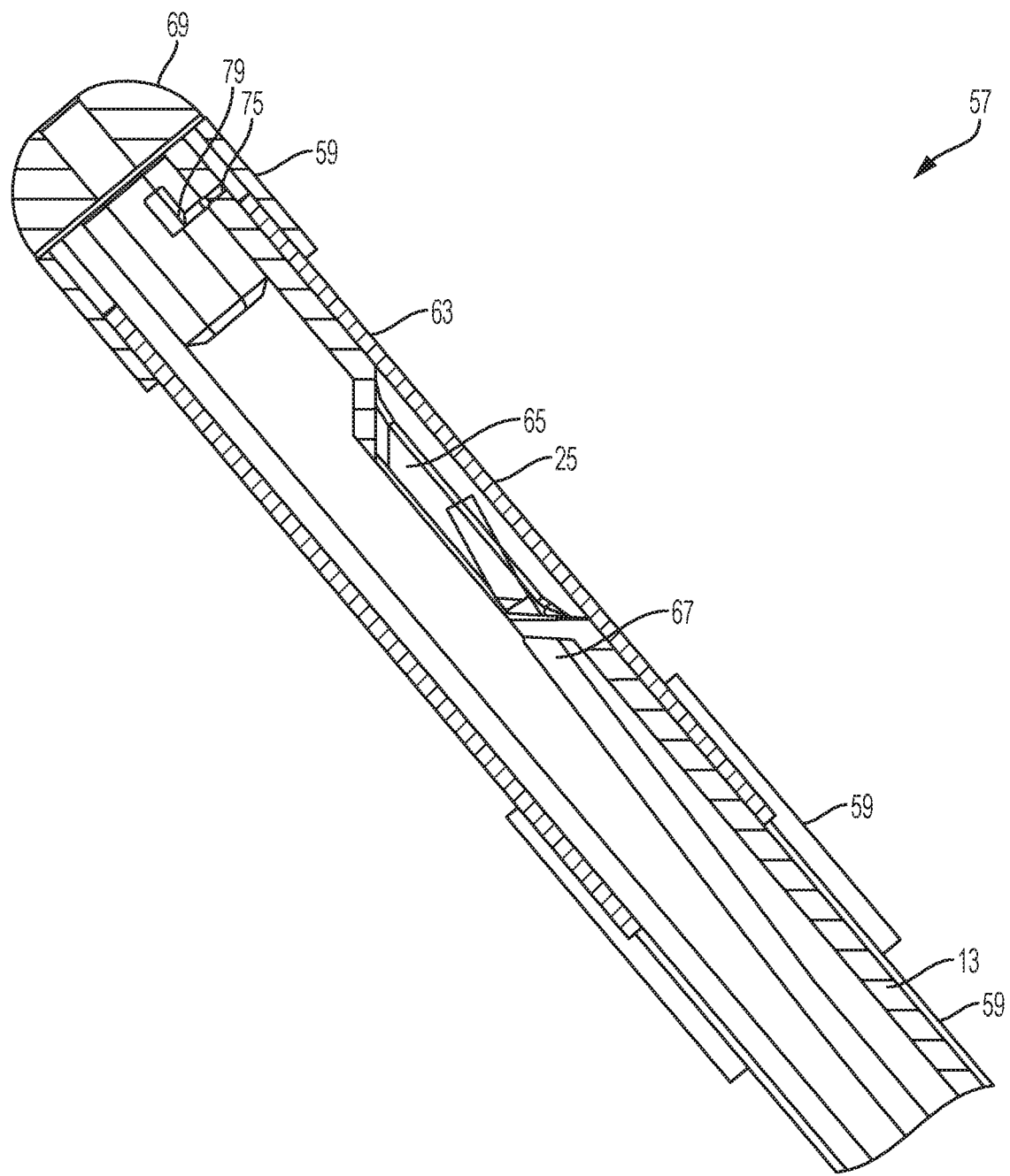
FIG. 6A is a schematic sectional representation of the most distal portion of the uterine manipulator device according to an embodiment.

Referring now to FIGS. 6A-6C, there are shown multiple views of schematic representations of the distal end 3 of the manipulator device 100. At distal end 3 of the manipulator device 100 is the most distal portion 57 of the manipulator tube 13. The most distal portion 57 of the manipulator tube 13 preferably has a diameter greater than that of the remaining portion of the manipulator tube 13 due to several features of the most distal portion 57 of the manipulator tube 13, discussed below.

Turning first to FIG. 6A, a sectional (along the longitudinal axis) schematic representation of the distal end 3 of the manipulator device 100 is shown. The intrauterine balloon 25 is shown positioned on the most distal portion of the manipulator tube 13. The balloon 25 (e.g., 10 cc inflatable balloon) is configured and positioned to reduce the risk of uterine perforation and is used to stabilize the manipulator tube 13 within the uterine cavity. The balloon 25 can be a Thermoplastic Elastomer (TPE) balloon. In one embodiment, the TPE balloon is based on a styrene block copolymer, SEBS compound. TPE balloons are similar to PVC balloons in strength and performance, and is composed and configured to maintain inflation of the balloon. Although a TPE balloon 25 is shown and described in conjunction with the uterine manipulator device 100, a conventional silicone or urethane based balloon may be used. However, TPE balloons are less permeable to gas as compared to silicone balloons. As silicone balloons are more permeable to gas, they can deflate. To combat deflation, saline is often used to inflate the silicone balloon as saline will not permeate. TPE balloons achieve similar performance by inflating the balloon with gas. Gas does not strain bonds in the balloon as much as saline, so gas is preferable if inflation can be maintained. However, TPE balloons can be used with saline, at the choice of the user.

Referring still to FIG. 6A, the intrauterine balloon 25 covers the manipulator tube 13 on its most distal portion 57. In conventional uterine manipulator devices, the balloon is glued in place on both the proximal and distal ends of the balloon (or other similar adhesive is used) to seal the balloon to the metal tube. In the embodiment shown in FIG. 6A, heat shrink 59 is used to cover the balloon on both the proximal and distal ends of the balloon over the manipulator tube 13. Any commercially available heat shrink for insulating a tube can be used. In one embodiment, Insultab's HS-714 (acrylated polyolefin) heat shrink can preferably be used. The heat shrink can be colored to facilitate visibility of the laser graduation markings. The heat shrink material sticks to itself and metal manipulator tube 13 very well, which makes it a superior form of adherence means relative to other conventional methods (e.g., adhesive). The inventors discovered that heat shrink 59 has many manufacturing and reliability advantages over the conventional use of adhesive. For example, the heat shrink 59 better retains its properties through the sterilization process as compared to adhesives. As adhesive degrades and weakens, the balloon may slide, causing patient exposure to the adhesive, and also may lead to malfunction of the balloon itself.

The heat shrink shown in FIGS. 6B and 6C, seals the intrauterine balloon 25 at a first position and a second position along the most distal portion 57 of the manipulator tube 13 forming a pair of collars 61 around the balloon 25. As shown in FIGS. 6A and 6C, the heat shrink is also used to cover the entirety of the manipulator tube 13 at the position of collars 61 for sterilization purposes. A portion 63 of the balloon 25 is not covered with heat shrink 59 so that the balloon 25 may inflate. Turning briefly back to FIG. 6A, the uncovered portion 63 of the balloon 25 is adjacent a substantially enclosed cavity 65 between the manipulator tube 13 and the balloon 25. A lumen 67 provides a pathway through the manipulator tube 13 to transport gas to the balloon 25 through the cavity 65. The lumen 67 provides a closed passage to the balloon 25 to facilitate inflation without introducing dye from the dye injection port 7 into the balloon 25.

Additionally shown in FIG. 6A-6C is a cap 69 at the most distal portion 57 of the manipulator tube 13. FIG. 6C shows that the cap 69 is approximately T-shaped, with a rounded portion 71 and a stem portion 73. FIG. 6A shows that the stem portion 73 of the cap 69 is positioned within the manipulator tube 13. The rounded portion 71 extends across the diameter of the most distal portion 57 of the manipulator tube 13. Specifically, the diameter of the rounded portion 71 of the cap 69 extends beyond the diameter of the manipulator tube 13 and out to a similar diameter of the heat shrink collar 61. In the depicted embodiment, a gap 75 is shown between a heat shrink collar 61 and the manipulator tube 13. However, when the heat shrink 59 is applied to the manipulator tube 13, the heat shrink 59 will deform and fill in the gap 75.

Turning back to FIG. 6C, the cap 69 additionally comprises a molded channel 77 for the passage of dye through both the rounded and stem portions 71, 73 of the cap 69. The channel 77 extends entirely through the cap 69 to facilitate the passage of dye therethrough. Dye can be passed from the dye injection port 7 at the proximal end 1 through the manipulator tube 13 and the cap 69 into the uterine cavity. Conventional caps are closed and utilize a slit in the balloon to create a passage for dye. The slit in the balloon is open during manufacturing and closed via a seal before use of the balloon. In some instances, the seal does not work and the slit remains open, which renders the balloon inoperable. In other instances, the closed cap causes adhesive to bunch up at the tip of the manipulator tube. However, the balloon 25 in the embodiment shown in FIG. 6A is entirely separate from the manipulator tube 13 due to the lumen 67. In particular, dye flows through the manipulator tube 13 and through channel 77 in the cap 69, while gas is configured to be separately passed through lumen 67 to expand the balloon 25.

Figure 6D:
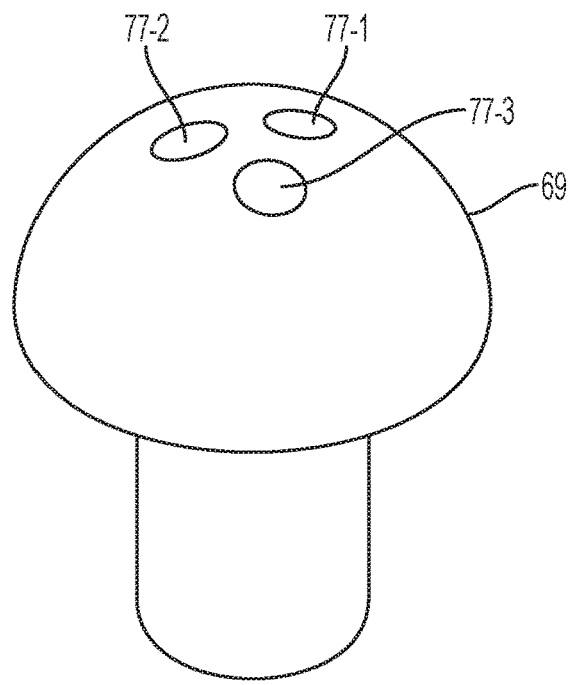
FIGS. 6D-6W are various views (perspective, top, bottom, and side) of alternative embodiments of a cap of a uterine manipulator device according to an alternative embodiment.
Figure 6E:
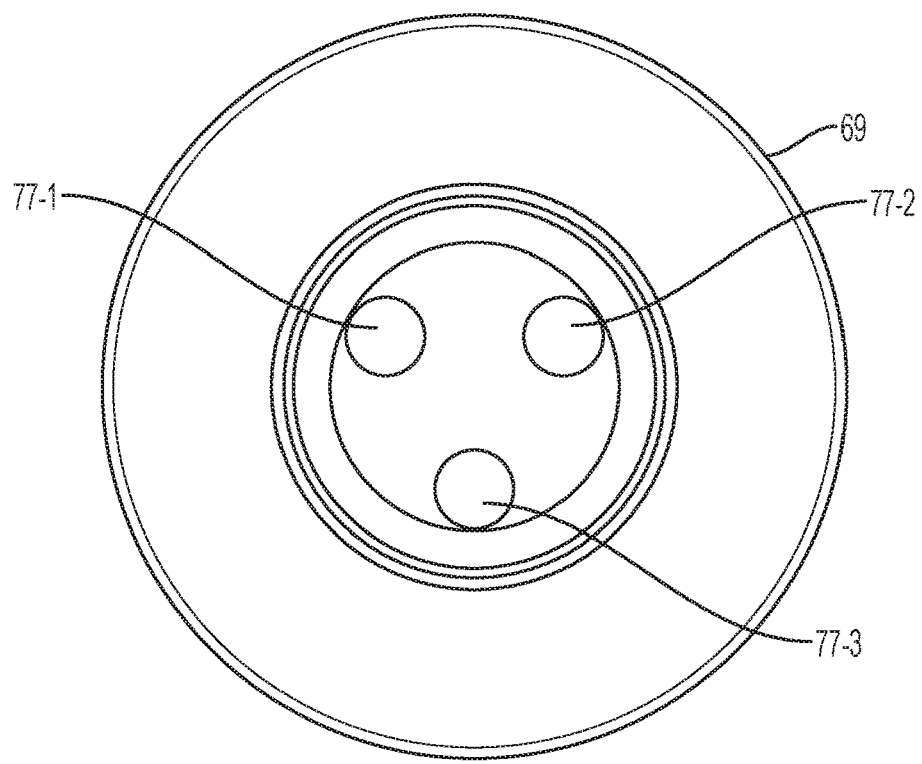
FIG. 6B is a top view of most distal portion of the uterine manipulator device according to an embodiment.
FIG. 6C is an exploded view of the most distal portion of the uterine manipulator device according to an embodiment.
Figure 6F:
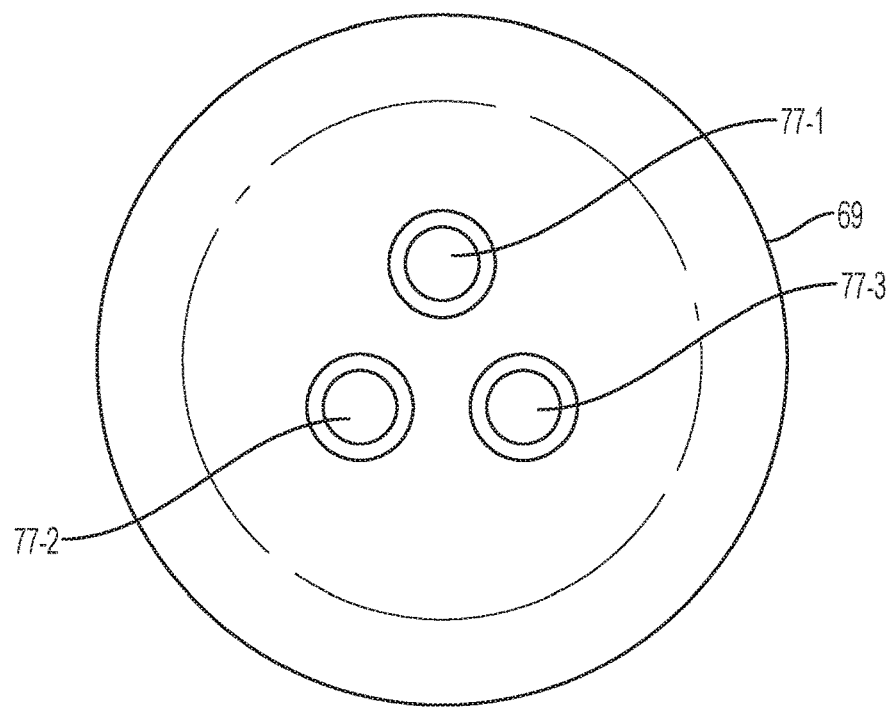
Figure 6G:
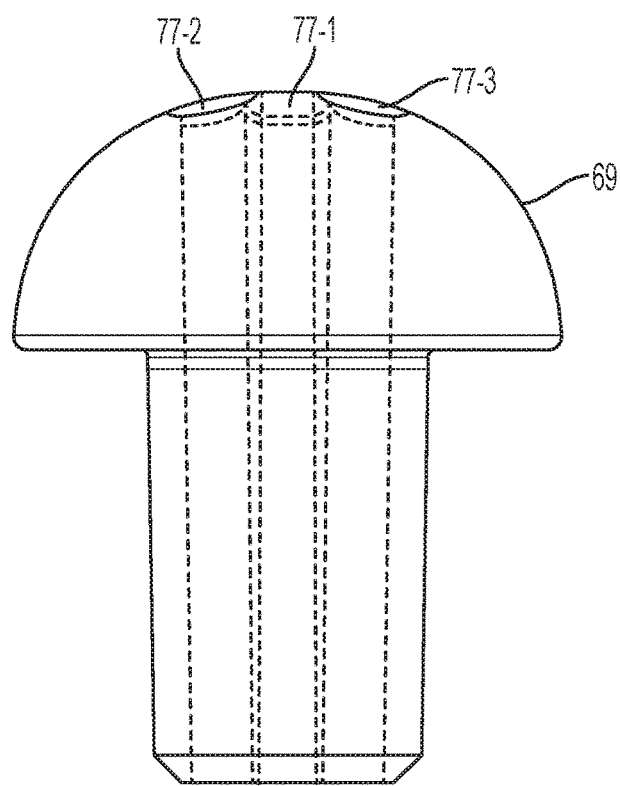
Figure 6H:
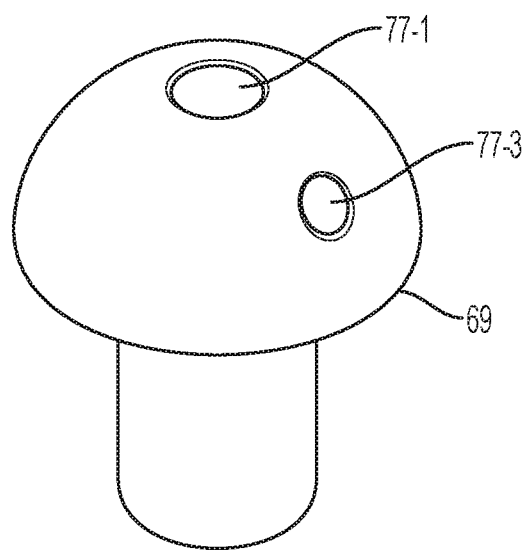
Figure 6I:
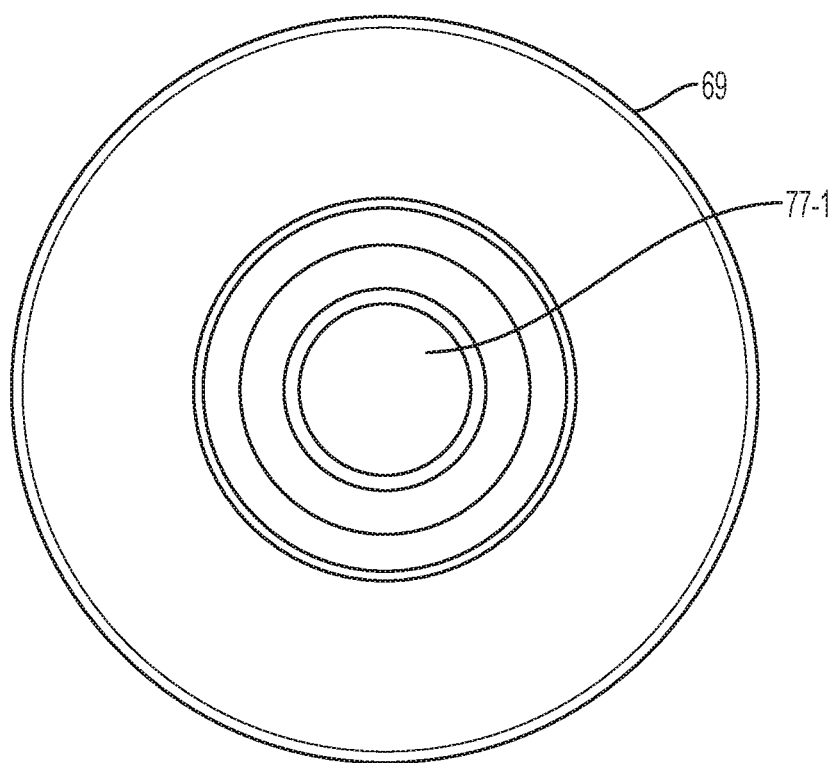
Figure 6J:
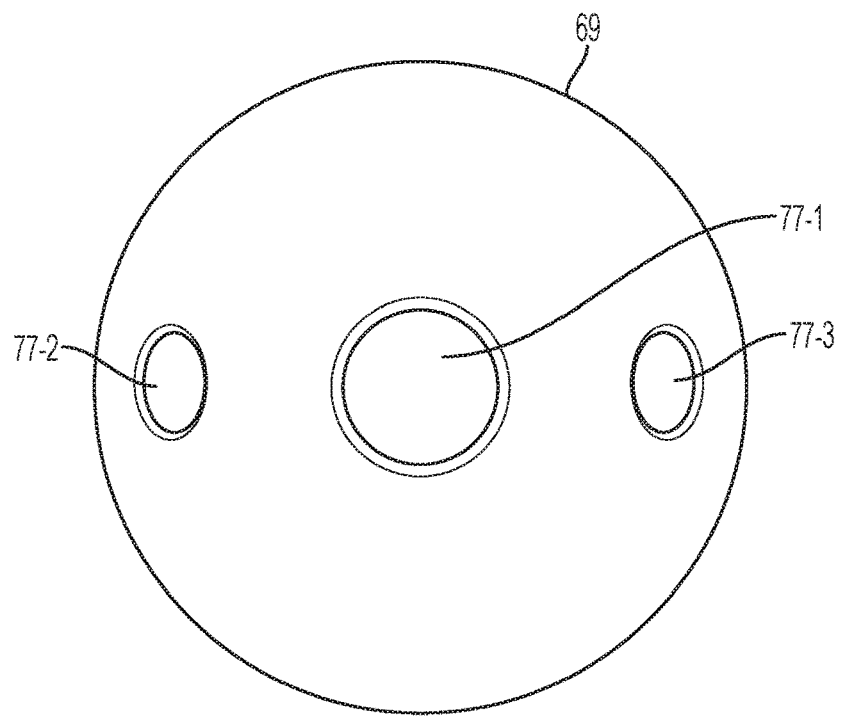
Figure 6K:
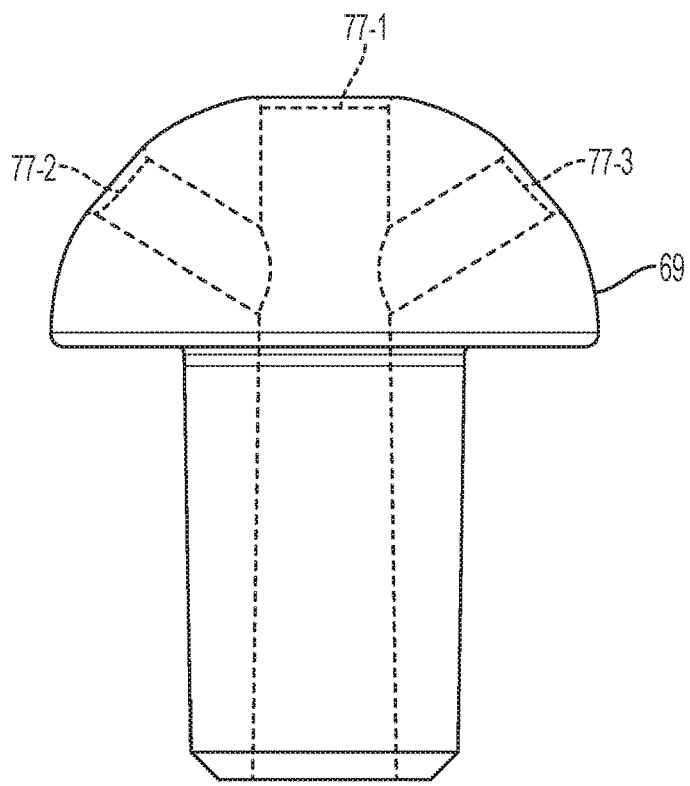
Figure 6L:
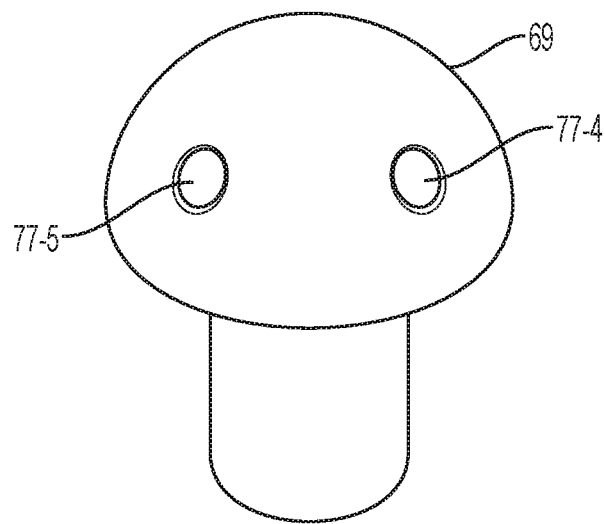
Figure 6M:
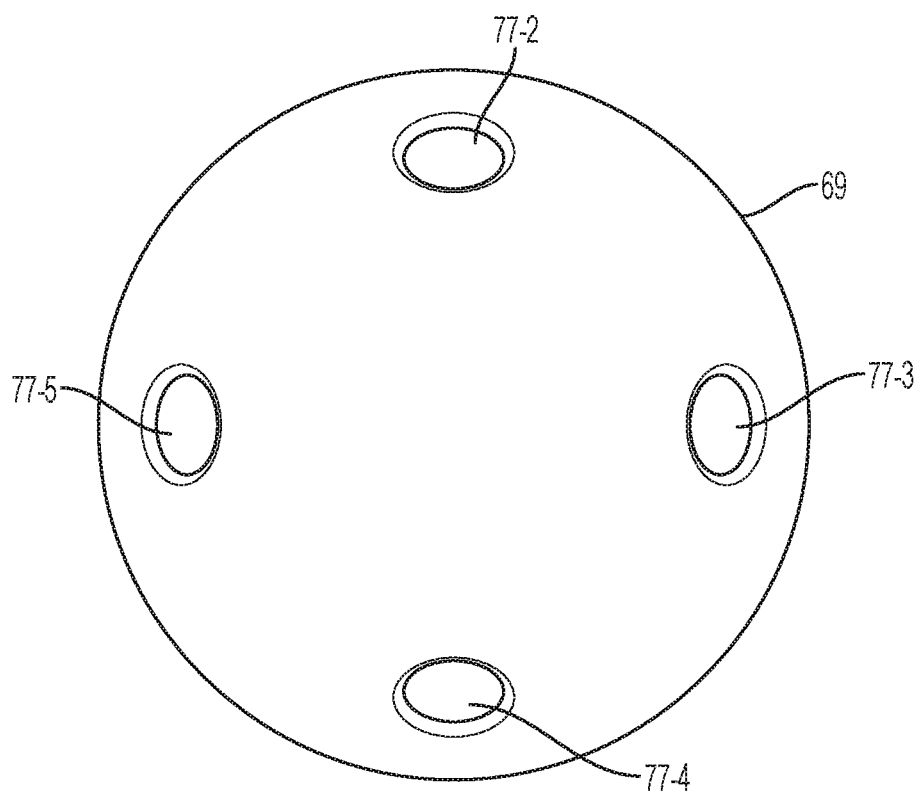
Figure 6N:
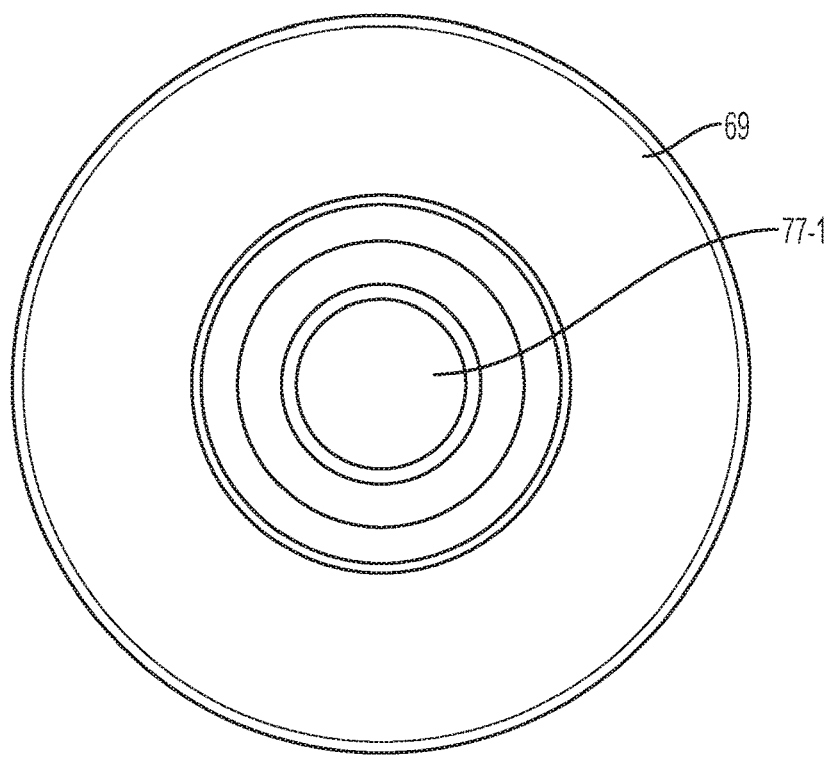
Figure 6O:
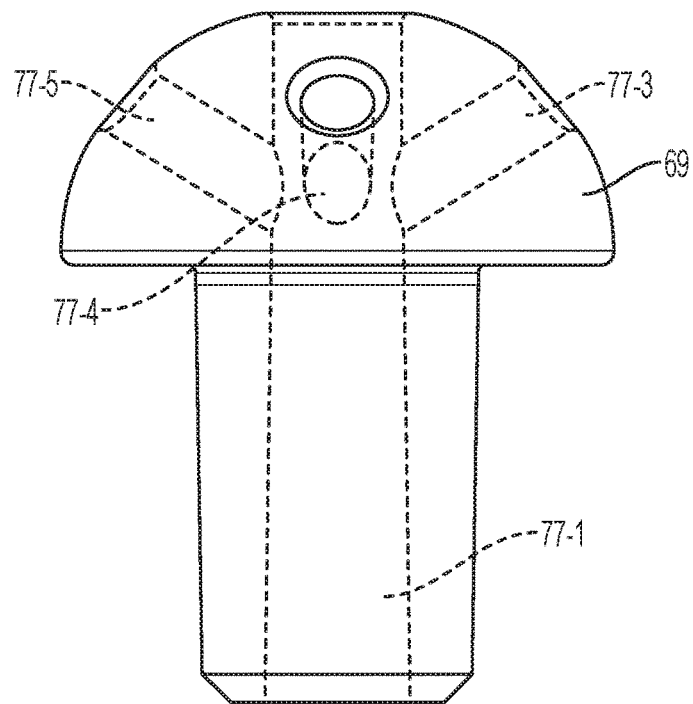
Figure 6P:
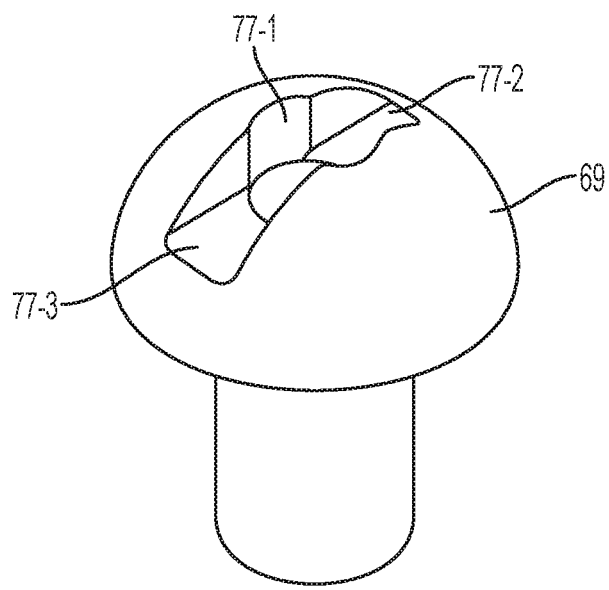
Figure 6Q:
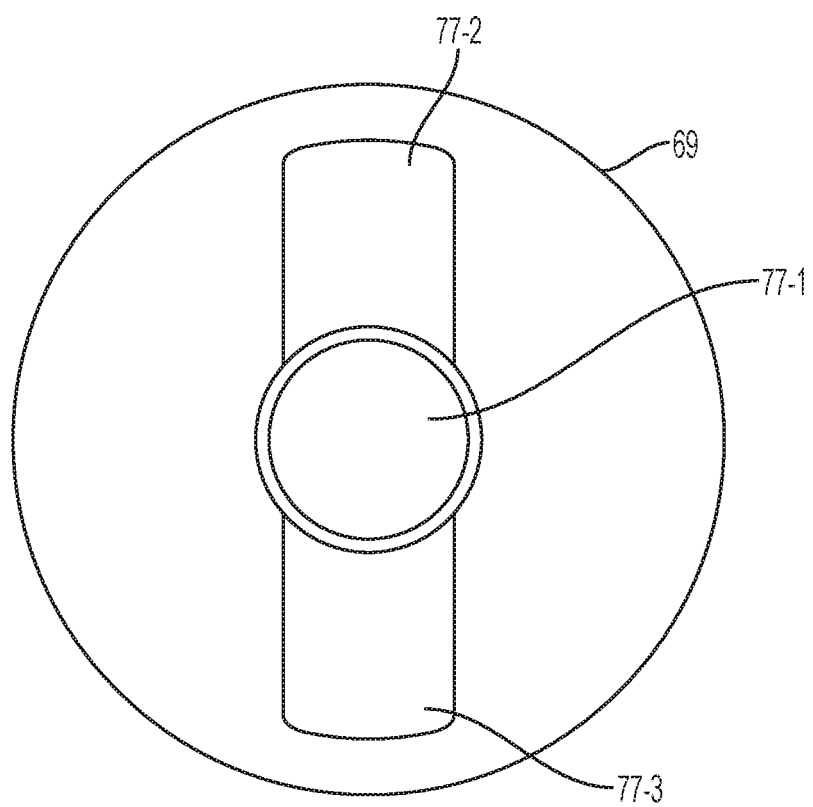
Figure 6R:
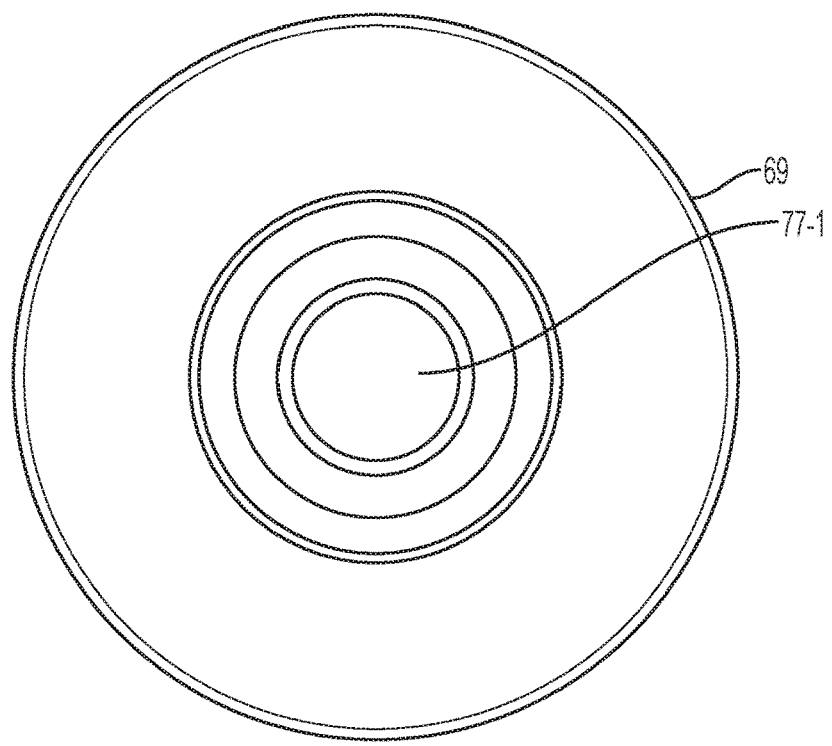
Figure 6S:
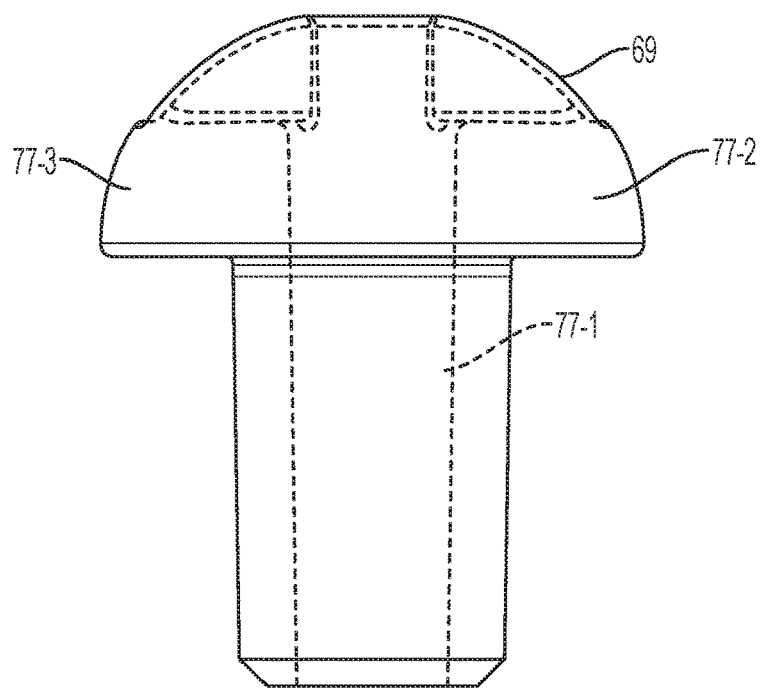
Figure 6T:
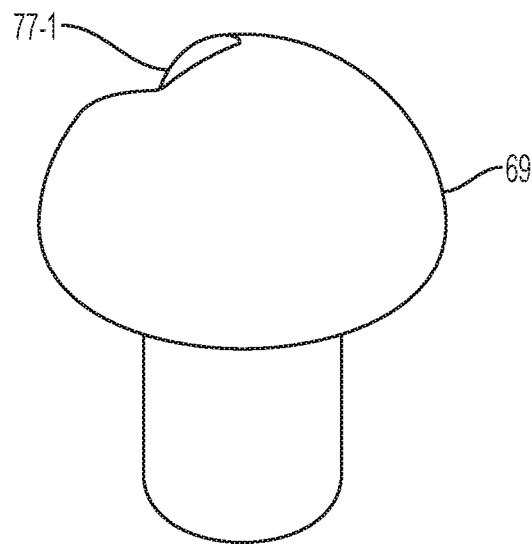
Figure 6U:
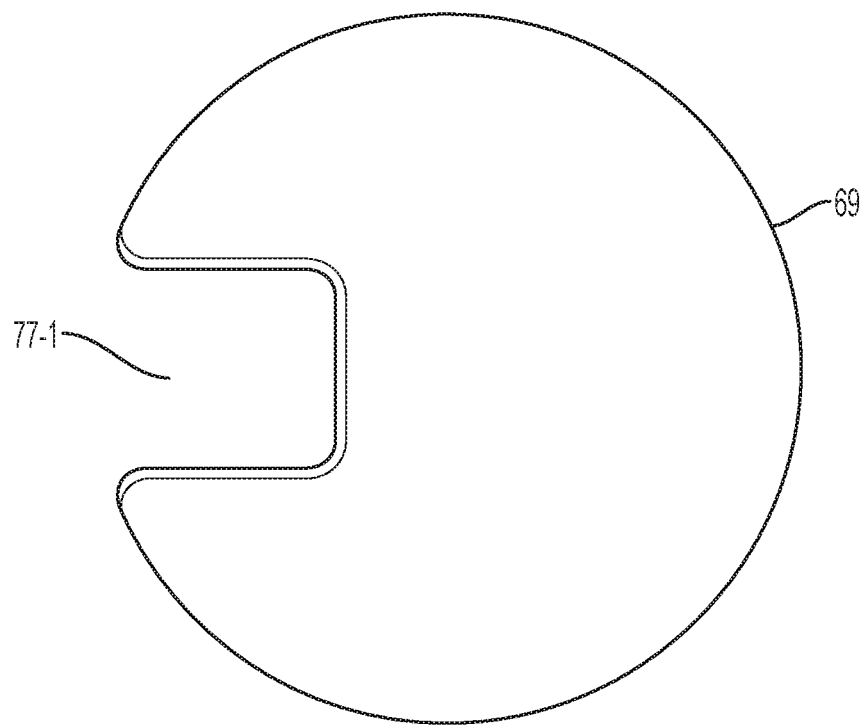
Figure 6V:
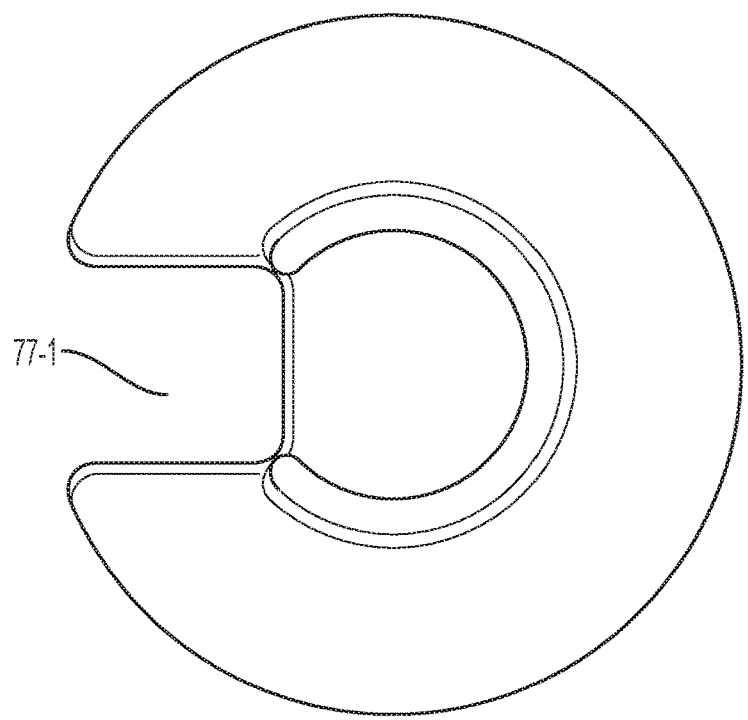
Figure 6W:
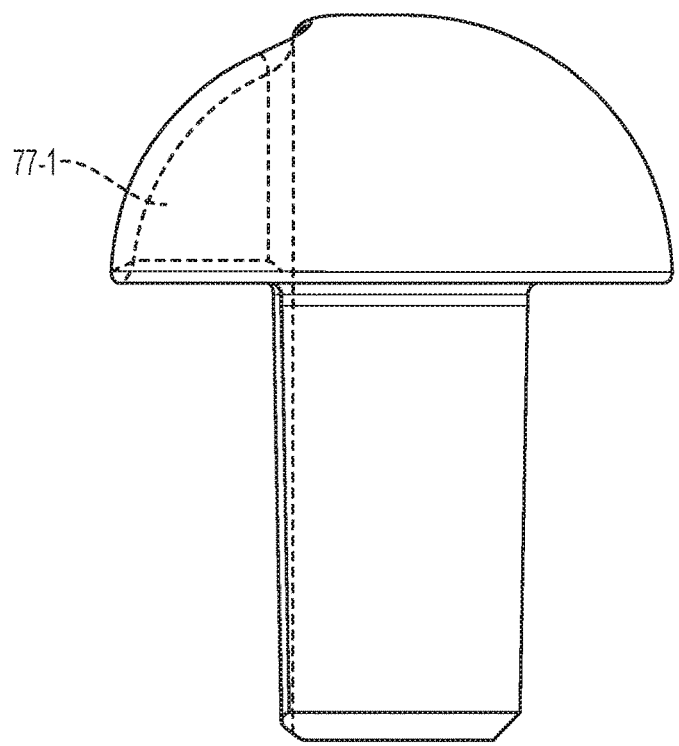

Turning to FIGS. 6D-6W, various views (perspective, top, bottom, and side) of alternative embodiments of cap 69 are illustrated. These alternative embodiments of cap 69 include various structural configurations and numbers of molded channels passing therethrough. For example, one or more channels can pass through the center of cap 69, on either side of cap 69, and can include bifurcations into additional multiple channels (which can assist with strategically distributing dye to certain anatomy, such as to and through the fallopian tubes).

Referring to FIGS. 6D-6G, various views of cap 69 are shown with multiple channels 77-1, 77-2, and 77-3 separately passing therethrough.

Referring to FIGS. 6H-6K, various views of cap 69 are shown with a main channel 77-1 that bifurcates into two additional channels 77-2 and 77-3.

Referring to FIGS. 6L-6O, various views of cap 69 are shown with a main channel 77-1 that bifurcates into four separate channels 77-2, 77-3, 77-4 and 77-5.

Referring to FIGS. 6P-6S, various views of cap 69 are shown with a main channel 77-1 that bifurcates into two additional open channels 77-2 and 77-3 on the top surface of cap 69.

Referring to FIGS. 6T-6W, various views of cap 69 are shown with a main open side channel 77-1, which, when in use, the side channel 77-1 is at least partially enclosed by the cannulated tube 13 (within which the proximal end of the cap 69 fits).

Figure 7:
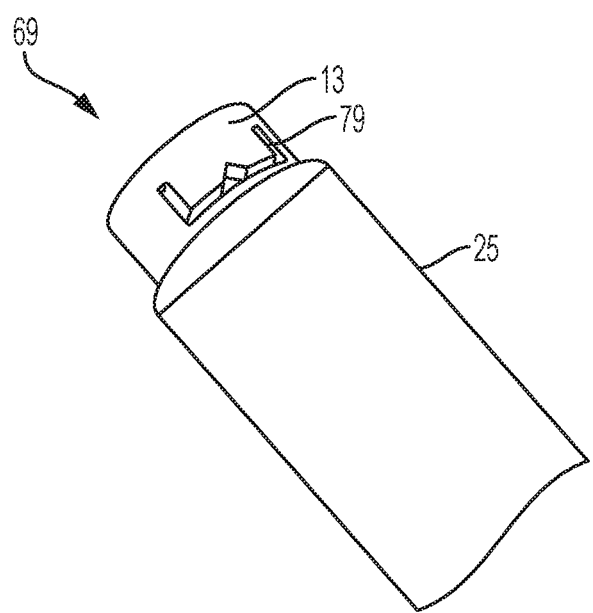
FIG. 7 is a close-up schematic representation of the most distal portion of the uterine manipulator device with the balloon removed according to an embodiment.

Referring now to FIG. 7, the cap 69 is shown at the most distal portion 57 of the manipulator tube 13 prior to application of the heat shrink 59. The manipulator tube 13 comprises a mechanical retaining feature 79 adjacent the cap 69. In the depicted embodiment, the retaining feature 57 is positioned between the cap 69 and the balloon 25. In the embodiment shown in FIG. 7, the retaining feature 79 is a "W" feature or dimpled tab laser cut in the manipulator tube 13. The "W" feature 79 captures the cap 69 on the inside of the manipulator tube 13 (as shown in FIG. 6A). Conventionally, adhesive, such as a gel adhesive, is used to secure the cap. However, adhesive can deteriorate and the cap can may become unattached and get lost in the patient. In accordance with an embodiment, adhesive can be used with the "W" feature to assist with the mechanical retaining as discussed above.

Figure 8:
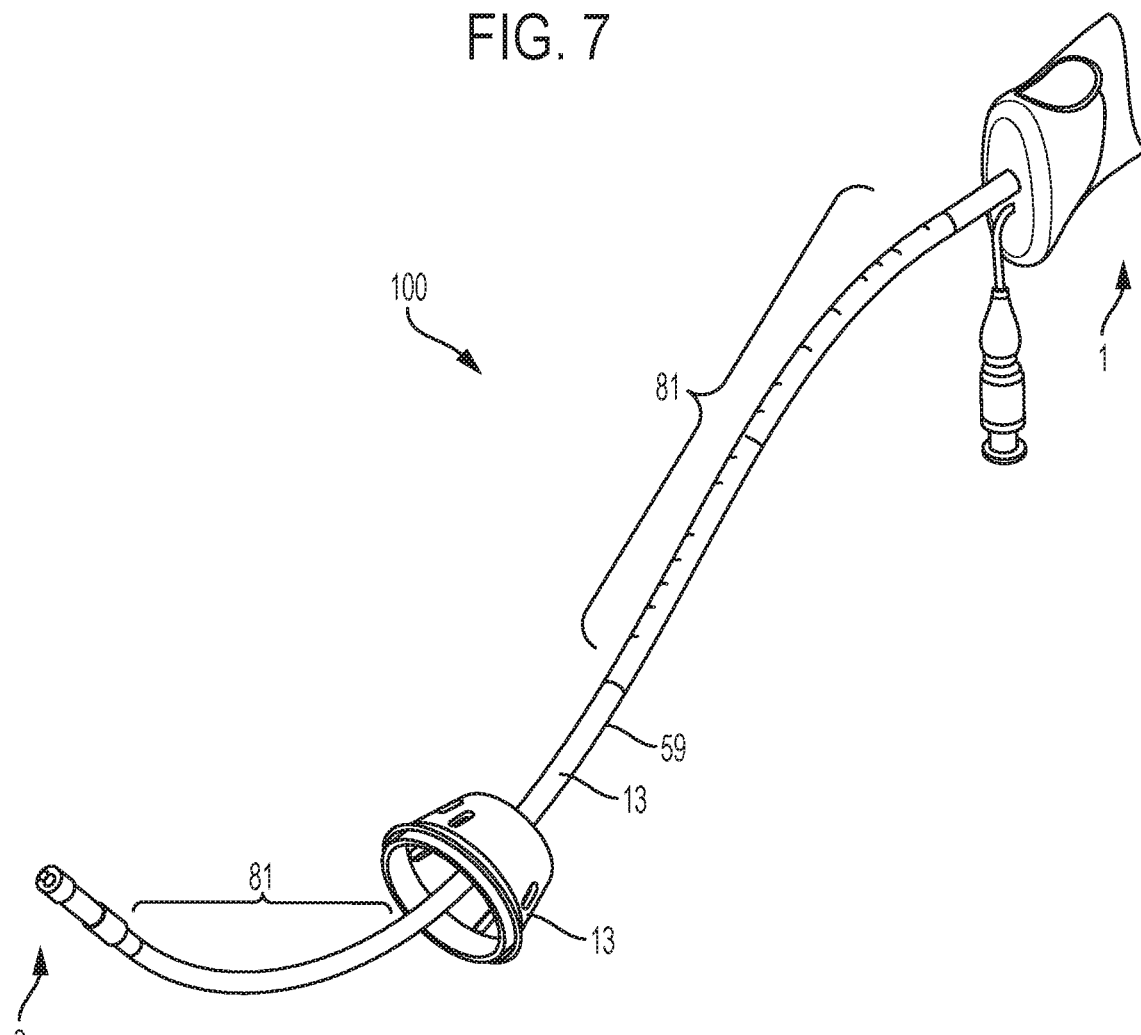
FIG. 8 is a top side perspective view of a uterine manipulator device with the occluder removed according to an embodiment.

Turning now to FIG. 8, there is shown side perspective view of the uterine manipulator device 100 with the occluder assembly 18 removed to show features of the manipulator tube 13. As shown in the depicted embodiment, the manipulator tube 13 has repeated sets of reference graduations 81 (e.g., 4 cm to 16 cm moving away from either side of the cervical cup 23). The manipulator tube 13 can be marked with reference graduations 81 from both the distal end 3 and the proximal end 1. The reference graduations 81 provide a guide for comparison to a graduated uterine sound, and can aid in attaining proper depth of insertion during use.

In conventional devices, reference graduations are added to the manipulator tube via the process of pad printing. Pad printing can be done prior to application of heat shrink. Although laser marking is typically cheaper than pad printing, it is more accurate and more permanent because, for example, pad printing can be rubbed off. Despite its benefits, laser marking has not been used on conventional uterine manipulator devices because conventional lasers, such as conventional fiber lasers or hybrid lasers, cannot laser mark heat shrink described as part of embodiments herein. However, in FIG. 8, the reference graduations 81 are laser marked on the manipulator tube 13. In one embodiment, the heat shrink 59 is first applied to the manipulator tube 13 before the reference graduations 81 are laser marked. It has been found and appreciated by the inventors that the acrylated heat shrink allows for an ultraviolet laser to mark the applied heat shrink layer. As such, in an embodiment, an ultraviolet laser is used to successfully mark a thin layer of the acrylated polyolefin on the manipulator tube 13. In such an embodiment, the UV laser emits a wavelength of 355 nm. It is contemplated that other wavelengths from the UV laser may be used to successfully create the reference graduations 81.

Figure 9A:
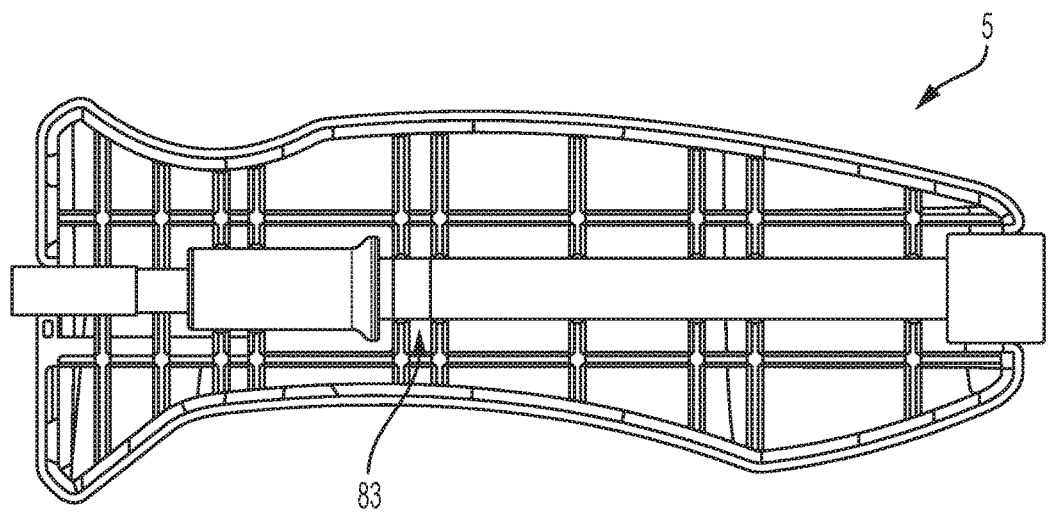
FIG. 9A is a schematic sectional representation of the handle of the uterine manipulator device according to an embodiment.
Figure 9B:
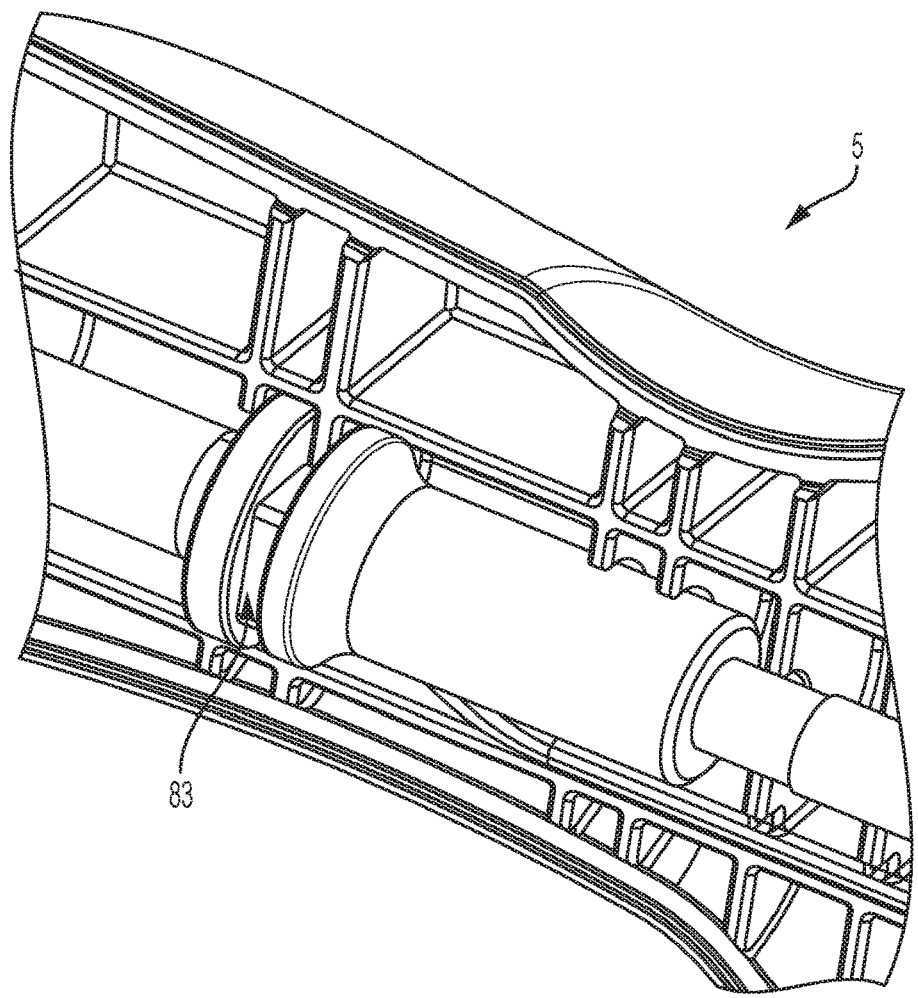
FIG. 9B is a close-up perspective sectional view of the handle of the uterine manipulator device according to an embodiment.

Turning now to FIGS. 9A-9B, there is shown a schematic representation and a perspective view of the handle 5 of the uterine manipulator device 100. The handle 5 has an anti-rotation feature that prevents the handle from torquing to allow for manipulation. In the depicted embodiment, the anti-rotation feature is a square overmolded key feature 83. Traditionally, the anti-rotation feature is a hexagonal shaped key feature. The hexagonal shape directed force in both the X and Y direction within the handle. Thus, two facets of the hexagonal shaped key feature would be seen at one time. With force in both the X and Y directions, the hexagonal shaped key feature is more likely to split open the handle when torqued. In the depicted embodiment, the square overmolded key feature 83 directs some force in only either the X or Y direction, not both. Therefore, the square overmolded key feature 83 is less likely to split open the handle 5.

The use of the uterine manipulator devices described herein are similar to the use of the uterine manipulator device described in US Pub. App. No. 20170354436 (see, e.g., FIG. 4, and para. [0028]).

While embodiments of the present invention has been particularly shown and described with reference to certain exemplary embodiments, it will be understood by one skilled in the art that various changes in detail may be effected therein without departing from the spirit and scope of the invention as defined by claims that can be supported by the written description and drawings. Further, where exemplary embodiments are described with reference to a certain number of elements it will be understood that the exemplary embodiments can be practiced utilizing either less than or more than the certain number of elements.

What is claimed is:

1. A uterine manipulator device comprising:
   an elongated cannulated tube comprising a proximal end and a distal end;

a cervical cup positioned on the elongated cannulated tube having a top distal portion of a first diameter and a base proximal portion of a second smaller diameter; and an occluder assembly comprising an occluder with a proximal end and a distal end positioned proximally from the cervical cup on the elongated cannulated tube, the occluder having a body with at least one primary rib and at least two secondary ribs, wherein a diameter of at least one secondary rib is smaller than the diameter of the primary rib; and wherein the occluder assembly further comprises a locking assembly positioned proximally from the occluder on the elongated cannulated tube, wherein the locking assembly is configured to lock the cervical cup and occluder from movement in at least one direction along the elongated cannulated tube; and wherein the locking assembly comprises a thumbscrew having a plurality of screw threads configured to lock into a collar, wherein at least one screw thread is deformed as compared to the other screw threads.

2. The device of claim 1, wherein at least a portion of the occluder is conically-shaped having a taper extending from one of the secondary ribs to the distal end of the occluder.

3. The device of claim 1, wherein the occluder is spheroid shaped such that one of the secondary ribs is positioned proximally to the primary rib and one of the secondary ribs is positioned distally to the primary rib.

4. The device of claim 1, wherein the occluder is composed of open cell foam.

5. The device of claim 1, wherein the body of the occluder comprises an outer skin layer having a different density than the remainder of the body.

6. The device of claim 5, wherein the outer skin layer has a first gas permeability and the remainder of the body has a second gas permeability.

7. The device of claim 1, wherein the occluder assembly further comprises an anti-occluder migration feature on at least one of a proximal side and a distal side of the occluder.

8. The device of claim 7, wherein the occluder assembly further comprises grooves positioned within the body of the occluder having a diameter of less than or equal to 50% of the rib having the smallest diameter.

9. The device of claim 7, wherein the occluder assembly further comprises grooves positioned within the body of the occluder having a diameter of less than or equal to 25% of the rib having the smallest diameter.

10. The device of claim 1, wherein the collar is composed of nylon.

11. A uterine manipulator device comprising:

an elongated cannulated tube comprising a proximal end and a distal end, wherein laser marked reference graduations are positioned along an outside surface of the elongated cannulated tube;

a cervical cup positioned on the elongated cannulated tube having a top distal portion of a first diameter and a base proximal portion of a second smaller diameter; and an occluder assembly comprising an occluder having a body positioned proximally from the cervical cup on the elongated cannulated tube; and wherein the occluder assembly further comprises a locking assembly positioned proximally from the occluder on the elongated cannulated tube, wherein the locking assembly is configured to lock the cervical cup and occluder from movement in at least one direction along the elongated cannulated tube; and wherein the locking assembly comprises a thumbscrew having a plurality of screw threads configured to lock into a collar, wherein at least one screw thread is deformed as compared to the other screw threads.

12. The device of claim 11, wherein the laser marked reference graduations extend both proximally and distally along the elongated cannulated tube from a location in between the proximal end and the distal end of the elongated cannulated tube.

13. The device of claim 11, wherein the reference graduations are laser marked with a UV laser emitting a wavelength of 355 nm.

14. The device of claim 11, wherein the reference graduations are laser marked on an acrylated polyolefin layer positioned over a surface of the elongated cannulated tube.

15. A uterine manipulator device comprising:

an elongated cannulated tube comprising a proximal end and a distal end;

a cervical cup positioned on the elongated cannulated tube having a top distal portion of a first diameter and a base proximal portion of a second smaller diameter; and an intrauterine balloon comprising a proximal end and a distal end and being positioned on the distal end of the elongated cannulated tube, wherein the proximal end and the distal end of the intrauterine balloon are secured to the elongated cannulated tube with heat shrink material; and an occluder assembly comprising an occluder having a body positioned proximally from the cervical cup on the elongated cannulated tube; and wherein the occluder assembly further comprises a locking assembly positioned proximally from the occluder on the elongated cannulated tube, wherein the locking assembly is configured to lock the cervical cup and occluder from movement in at least one direction along the elongated cannulated tube; and wherein the locking assembly comprises a thumbscrew having a plurality of screw threads configured to lock into a collar, wherein at least one screw thread is deformed as compared to the other screw threads.

16. The device of claim 15, further comprising a handle positioned on the proximal end of the elongated cannulated tube.

17. The device of claim 16, further comprising an inflation valve positioned through the handle and communicatively coupled to a gas passage lumen in the elongated cannulated tube.

18. The device of claim 17, further comprising an enclosed cavity positioned between the elongated cannulated tube and the intrauterine balloon, and which communicatively connects to the gas passage lumen.

19. The device of claim 16, further comprising a dye injection port positioned through the handle and communicatively coupled to the elongated cannulated tube and a cap positioned on the distal end of the elongated cannulated tube.

20. The device of claim 19, wherein the elongated cannulated tube further comprises a mechanical retaining feature configured to secure the cap to the elongated cannulated tube.

21. The device of claim 19, wherein the cap comprises a proximal end and a distal end, and at least one channel passing therethrough.

22. The device of claim 21, wherein the at least one channel extends through a side of the cap from the proximal end to the distal end of the cap.

23. The device of claim 21, wherein the at least one channel is centrally positioned within the cap and extends between the distal end and the proximal end of the cap.

24. The device of claim 23, wherein the at least one channel bifurcates into at least one additional channel.

25. The device of claim 16, further comprising a square key feature in the handle which directs an applied force in one direction only.

26. The device of claim 15, wherein the intrauterine balloon is composed of a thermoplastic elastomer.

27. A method of manufacturing the uterine manipulator device of claim 1, further comprising the elongated cannulated tube with an outside surface, comprising the steps of:
    applying a layer of heat shrink to the outside surface of the elongated cannulated tube, and applying laser mark reference graduations along an outside surface of the heat shrink on the elongated cannulated tube.

28. The method of claim 27, wherein the laser mark reference graduations are applied using a UV laser emitting a wavelength of 355 nm.

29. The method of claim 27, wherein the heat shrink layer comprises an acrylated polyolefin layer.

* * * * *